United States Patent [19]
Craig et al.

[11] Patent Number: 5,610,174
[45] Date of Patent: Mar. 11, 1997

[54] USE OF $\alpha_{1A}$-SELECTIVE ADRENOCEPTOR AGONISTS FOR THE TREATMENT OF URINARY INCONTINENCE

[75] Inventors: Douglas A. Craig, Fair Lawn; Carlos C. Forray, Paramus; Charles Gluchowski, Wayne; Theresa A. Branchek, Teaneck, all of N.J.

[73] Assignee: Synaptic Pharmaceutical Corporation, Paramus, N.J.

[21] Appl. No.: 459,410

[22] Filed: Jun. 2, 1995

[51] Int. Cl.$^6$ .................. A61K 31/415; A61K 31/18; A61K 31/40; A61K 31/405

[52] U.S. Cl. .................. 514/401; 514/402; 514/400; 514/396; 514/605; 514/394; 514/414; 514/415; 514/418; 514/452; 514/466

[58] Field of Search .................. 514/400, 396, 514/402, 605, 394, 414, 415, 418, 452, 466, 401

[56] References Cited

U.S. PATENT DOCUMENTS 4,634,705  1/1987  DeBernardis et al. .................. 514/256

OTHER PUBLICATIONS

Forray, Carlos et al., "The Alpha1–Adrenergic Receptor that Mediates Smooth Muscle Contraction in Human Prostate has the Pharmacological Properties of the Cloned Human Alpha1c Subtype," Molecular Pharmacology (1994), vol. 45, pp. 703–708.

Hatano, Akihiko et al., "Pharmacological evidence of distinct Alpha1–Adrenoceptor subtypes mediating the contraction of human prostatic urethra and peripheral artery," British Journal of Pharmacology (1994), vol. 113, pp. 723–727.

Testa, Rodolfo et al., "Characterization of Alpha1–Adrenoceptor subtypes in prostate and prostatic urethra of rat, rabbit, dog and man," European Journal of Pharmacology (1993), vol. 249, pp. 307–315.

Watson, Steve and Girdlestone, Debbie, "1995 Receptor & Ion Channel Nomenclature Supplement—Trends in Pharmacological Sciences," Trends in Pharmacological Sciences (1995) Sixth Edition, pp. 1–13.

Kyncl et al, *Chemical Abstracts*, vol. 110, No. 17, Abstract No. 14763v, 1989.

Kontani et al, *Chemical Abstracts*, vol. 117, No. 1, Abstract No. 576b, 1992.

*Primary Examiner*—Kimberly Jordan
*Assistant Examiner*—William R. A. Jarvis
*Attorney, Agent, or Firm*—John P. White

[57] ABSTRACT

The present invention provides a method of treating urinary incontinence in a subject which comprises administering to the subject a therapeutically effective amount of a compound having the following structure:

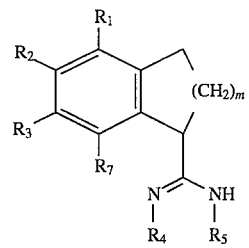

wherein each of the substiutents for the compound is as defined in the specification.

3 Claims, 6 Drawing Sheets

SK&F 102652

A-61603

SDZ NVI 085

Prazosin Hydrochloride

5-Methyl Urapidil

Abanoquil Hemifumarate Hydrate

Compound 1

ST-1059

USE OF $\alpha_{1A}$-SELECTIVE ADRENOCEPTOR AGONISTS FOR THE TREATMENT OF URINARY INCONTINENCE Throughout this application, various references are referred to within parentheses. Disclosures of these publications in their entireties are hereby incorporated by reference into this application to more fully describe the state of the art to which this invention pertains. Full bibliographic citations for these references may be found immediately preceding the claims.

BACKGROUND OF THE INVENTION

The designation "$\alpha_{1A}$" is the appellation recently approved by the IUPHAR Nomenclature Committee for the previously designated "$\alpha_{1C}$" cloned subtype as outlined in the 1995 Receptor and Ion Channel Nomenclature Supplement (Watson and Girdlestone, 1995). However, the designation $\alpha_{1C}$ is used throughout this application and the supporting tables and figures to refer to the receptor subtype recently renamed "$\alpha_{1A}$". Since in both the old and new nomenclature there has only been one unique receptor subtype which has been designated $\alpha_{1C}$ (i.e., there is no $\alpha_{1C}$ under the current nomenclature), "$\alpha_{1C}$" is an unambiguous description of this unique receptor subtype.

Incontinence is a condition characterized by the involuntary loss of urine. It can be divided generally into two types, the first involving an unstable bladder as the underlying cause, and the second involving an insufficiency in bladder outlet closing pressure despite the presence of a stable bladder. The condition may arise from a variety of different pathological, anatomical or neurological factors (Lundberg, 1989).

While the prevalence in females is two fold higher, it also affects males (Lundberg, 1989). The greatest incidence is seen in postmenopausal women. It is estimated that at least 10 million Americans suffer from urinary incontinence (Sand et al., 1990). Incontinence can be treated by surgical and nonsurgical methods. Conservative approaches include physiotherapy (Kegel exercises) and functional electrical stimulation which aim to strengthen the peri-urethral musculature (Walters et al., 1992). Periurethral injection of polytetraflurorethylene is a more invasive procedure intended to augment the urethral support (Sand et al, 1990). The most radical treatment for stress incontinence is surgery, involving a variety of techniques which seek to improve the alignment of the bladder, urethra, and surrounding structures.

A variety of pharmaceutical agents have been employed with varying success to treat urinary incontinence. Drugs useful in reducing the contractility of the bladder include anticholinergics, β-blockers, calcium channel blockers, and tricyclic antidepressants. Estrogen has been used with some success in increasing bladder outlet resistance, particularly in postmenopausal women. Its actions have been attributed to a "mucosal seal effect" resulting from urethral mucosal cell proliferation (Wein, 1987), although there is now some suggestion that it may also contribute to a restoration of α-adrenoceptor expression in the urethra (Wein, 1987).

The most commonly employed agents for increasing bladder outlet resistance are the α-adrenoceptor agonists. These activate α-adrenoceptors located on the smooth muscle cells of the proximal urethra and bladder neck (Sourander, 1990; Wein, 1987), resulting in contraction and increased closing pressure. The compounds currently employed for this therapy include the non-selective adrenoceptor agents phenylpropanolamine, ephedrine, and phenylephrine (Wein, 1987; Lundberg, 1989). The actions of these drugs are attributable, in part, to direct activation of adrenoceptors and in part to their ability to displace endogenous norepinephrine from sympathetic neurons following uptake into the nerve terminal, a so-called indirect sympathomimetic action (Andersson and Sjögren, 1982). Their lack of selectivity (see Table 3 hereinafter) among the adrenoceptor subtypes and the indirect action of these compounds results in their activating $\alpha_1$-, $\alpha_2$-, and β-adrenoceptors in the CNS and in the periphery. As a result, any desired therapeutic effect of these agents may be accompanied by a constellation of undesirable side effects. One major side effect of their use in incontinence is an increase in blood pressure. This effect is dose-dependent and limits the ability to achieve therapeutically effective circulating concentrations of the drug (Andersson and Sjögren, 1982). In addition, these compounds in some patients produce insomnia, anxiety and dizziness as a result of their stimulant actions in the CNS (Andersson and Sjögren, 1982, Wein, 1987).

Another compound which has been evaluated in urinary incontinence is midodrine, a prodrug which is converted in vivo to the active phenylethylamine ST-1059. The clinical efficacy of midodrine has not been demonstrated conclusively (Andersson and Sjögren, 1982). Like the above compounds, its effects may be limited by cross-reactivity with other adrenoceptors (see Table 3) which may limit the maximum achievable dose. A better understanding of the subtypes of α-adrenoceptors and their involvement in various physiological processes will facilitate the development of more efficacious drugs for the treatment of incontinence. The α-adrenoceptors are specific neuroreceptor proteins located in the peripheral and central nervous systems and on tissues throughout the body. The receptors are important switches for controlling many physiological functions and, thus, represent important targets for drug development. Drugs which interact at these receptors comprise two main classes: agonists, which mimic the endogenous ligands (norepinephrine and epinephrine) in their ability to activate the receptor; and antagonists, which serve to block the actions of the endogenous ligands. Many α-adrenoceptor drugs of both classes have been developed over the past 40 years. Examples in addition to those indicated above, which owe at least part of their action to stimulation of alpha adrenoceptors, include clonidine (agonist; treatment of hypertension), prazosin (antagonist; hypertension), oxymetazoline (agonist, nasal decongestion), and methoxamine (treatment of episodes supraventricular tachycardia). While many of these drugs are effective, they also produce undesirable side effects at therapeutic doses (e.g., clonidine produces dry mouth, sedation and orthostatic hypotension in addition to its antihypertensive effect). During the past 15 years a more precise understanding of α-adrenoceptors and drugs targeting α-adrenoceptors has emerged. Prior to 1977, only one α-adrenoceptor was known to exist. Between 1977 and 1988, it was accepted by the scientific community that at least two α-adrenoceptors, $\alpha_1$ and $\alpha_2$, existed in the central and peripheral nervous systems. Since 1988, new techniques in molecular biology have led to the identification of at least six distinct α-adrenoceptor proteins which are distributed throughout the central and peripheral nervous systems: $\alpha_{1A}$, $\alpha_{1B}$, $\alpha_{1C}$, $\alpha_{2A}$, $\alpha_{2B}$ and $\alpha_{2C}$ (Bylund, 1992). In addition to the cloned α-adrenoceptors, several putative $\alpha_1$ adrenoceptor subtypes have been recently described based upon functional studies in a variety of mammalian tissues. These receptors, which have not been cloned, are described as $\alpha_{1H}$, $\alpha_{1L}$ and $\alpha_{1N}$ (Murmamatsu, 1995) or "atypical $\alpha_1$" (Abel, 1995) adrenoceptors. The precise role of each of the subtypes in various physiological responses is only beginning to be understood, but it is clear that distinct subtypes do mediate distinct physiological responses to agonists and antagonists. For example, it has been shown that norepinephrine-induced contractions of the human prostate are mediated by the $\alpha_{1C}$-adrenoceptor (Forray et al., 1994). Many adrenoceptor drugs developed before 1992 are not selective for any particular $\alpha$-adrenoceptor subtype. It is increasingly evident that this lack of receptor subtype selectivity is an underlying cause of the untoward side-effects of these drugs.

The role of the sympathetic adrenergic nervous system in the storage function of the bladder is well recognized (Wein, 1987; Latifpour et al, 1990). Likewise, it is understood in the art that the study of adrenoceptor mechanisms in isolated urethra and bladder tissues is applicable to incontinence therapy (Latifpour et al., 1994; Tsujimoto et al., 1986). Various groups have attempted to identify, through binding and functional studies, $\alpha_1$ receptor subtypes in the urethrae of humans, rabbits, and rats (Yoshida et al., 1991; Testa et al. 1993; Chess-Williams et al., 1994). These efforts have, thus far, failed to provide conclusive evidence for a particular $\alpha_1$-adrenoceptor subtype being responsible for the effects of adrenoceptor agonists in the urethra.

This invention relates to the discovery that $\alpha_{1C}$-agonists are useful for the treatment of urinary incontinence with the potential for decreased side effects. Data already exists which indicates that the $\alpha_{1C}$-adrenoceptor is not involved significantly in the cardiovascular actions of $\alpha$-agonists and antagonists (Forray et al., 1994). Therefore, agonists exhibiting significant binding and functional selectivity for the $\alpha_{1C}$-adrenoceptor over other $\alpha_1$-adrenoceptors, $\alpha_2$-adrenoceptors, $\beta$-adrenoceptors, as well as histamine receptors and serotonin (5-HT) receptors, are contemplated to be more effective agents, relative to currently available therapies, for the treatment of urinary incontinence.

SUMMARY OF THE INVENTION

The present invention provides a method of treating urinary incontinence in a subject which comprises administering to the subject a therapeutically effective amount of a compound having one of the following structures:

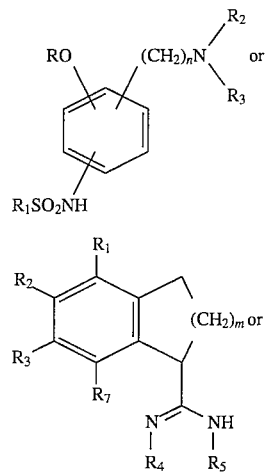

-continued

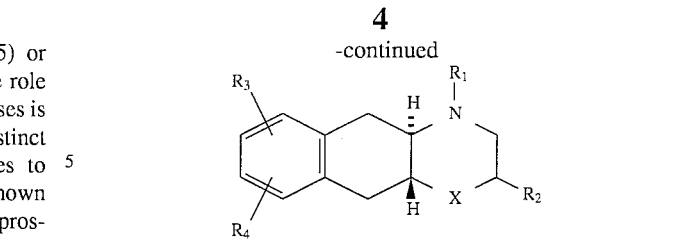

each of the substiutents for the compounds are as defined in the specification.

DETAILED DESCRIPTION OF THE INVENTION

Figure 1A:
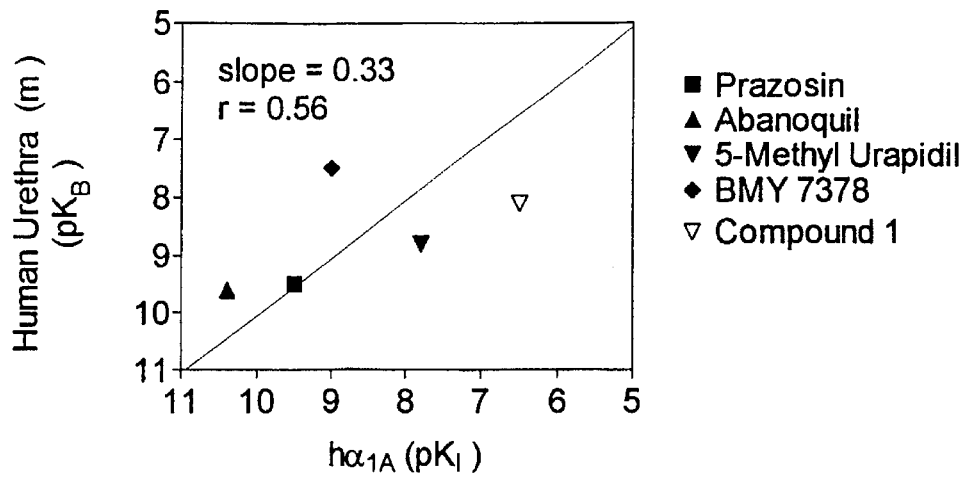
FIGS. 1A, 1B, and 1C show correlation of antagonist $pK_B$ values determined in functional studies of human urethra versus $pK_I$ values measured in binding experiments using cloned human $\alpha_{1A}$-adrenoceptors (A), $\alpha_{1B}$-adrenoceptors (B), and $\alpha_{1C}$-adrenoceptors (C). The slopes and correlation coefficients (r) for the linear regression analysis are presented in each figure.

The following definitions are presented as an aid in understanding this invention.

Receptor Activation describes the process in which the binding of a compound to the receptor when it is on the surface of a cell leads to a metabolic response within the cell. Such metabolic responses include, but are not limited to, activation of adenylyl cyclase, activation of guanylyl cyclase, hydrolysis of inositol phospholipids, movement of ions across the cell membrane, or contraction in a tissue in the cells of which the receptor is expressed.

Potency means the concentration of an agonist which elicits half of its maximum activation (expressed as $EC_{50}$, or the negative log of the $EC_{50}$, i.e., $pEC_{50}$).

Intrinsic Activity means the magnitude of the maximum activation in a cell or tissue which a particular agonist is capable of eliciting, relative to the maximum activation elicited by a reference full agonist and is expressed as values ranging between unity for full agonists (e.g., norepinephrine in the case of α-adrenoceptors) and zero for antagonists. Because intrinsic activity as originally defined (Ariens, 1960) is recognized as being dependent upon the receptor system in which it is measured (Kenakin, 1987), intrinsic activity herein is based upon measurements made using the cloned receptor systems described below.

Selectivity of Receptor Activation refers to the ability of an agonist to selectively activate one receptor relative to another receptor. Such selectivity may reflect either (a) the agonist's ability to activate one receptor at a much lower concentration than that required to activate another receptor (i.e., a potency difference) or (b) the agonist's ability to activate one receptor to a much greater degree than another receptor, independent of concentration, (i.e., an intrinsic activity difference) or (c) a combination of both.

Therefore, statements of the form "activates a human $\alpha_{1C}$-adrenoceptor at least ten-fold more than it activates any of the following (receptors)" mean and include any such difference whether it is by virtue of a difference in potency, or a difference in intrinsic activity, or both.

Having due regard to the preceding definitions, the present invention provides a method of treating urinary incontinence in a subject which comprises administering to the subject a therapeutically effective amount of an $\alpha_{1C}$ selective agonist which activates a human $\alpha_{1C}$ adrenoceptor at least ten-fold more than it activates a human $\alpha_{1A}$ adrenoceptor and a human $\alpha_{1B}$ adrenoceptor.

The invention further provides a method of treating urinary incontinence in a subject which comprises administering to the subject a therapeutically effective amount of an $\alpha_{1C}$ selective agonist which activates a human $\alpha_{1C}$ adrenoceptor at least 50-fold more than it activates a human $\alpha_{1A}$ adrenoceptor and a human $\alpha_{1B}$ adrenoceptor.

The invention provides a method of treating urinary incontinence in a subject which comprises administering to the subject a therapeutically effective amount of an $\alpha_{1C}$ selective agonist which activates a human $\alpha_{1C}$ adrenoceptor at least 100-fold more than it activates a human $\alpha_{1A}$ adrenoceptor and a human $\alpha_{1B}$ adrenoceptor.

The invention provides a method of treating urinary incontinence in a subject which comprises administering to the subject a therapeutically effective amount of an $\alpha_{1C}$ selective agonist which activates a human $\alpha_{1C}$ adrenoceptor at least 200-fold more than it activates a human $\alpha_{1A}$ adrenoceptor and a human $\alpha_{1B}$ adrenoceptor.

The $\alpha_{1C}$ selective agonist used to practice the method of treating urinary incontinence further has the characteristic that it does not antagonize a human $\alpha_{1A}$ adrenoceptor and a human $\alpha_{1B}$ adrenoceptor.

Desirably, the $\alpha_{1C}$ selective agonist used to practice the method of treating urinary incontinence activates the human $\alpha_{1C}$ adrenoceptor at least ten-fold more than it activates any human $\alpha_2$ adrenoceptor and any β adrenoceptor. Some examples of $\alpha_2$ adrenoceptors include the $\alpha_{2A}$, $\alpha_{2B}$, and $\alpha_{2C}$ receptors.

The invention also provides that the $\alpha_{1C}$ selective agonist used to practice the method of treating urinary incontinence further has the characteristic that it does not antagonize any human $\alpha_2$ adrenoceptor and any β adrenoceptor. Some examples of $\alpha_2$ adrenoceptors include the $\alpha_{2A}$, $\alpha_{2B}$, and $\alpha_{2C}$ receptors.

Desirably, the $\alpha_{1C}$ selective agonist used to practice the method of treating urinary incontinence activates the human $\alpha_{1C}$ adrenoceptor at least ten-fold more than it activates a human histamine $H_1$ or $H_2$ receptor.

The invention further provides that the $\alpha_{1C}$ selective agonist used to practice the method of treating urinary incontinence activates the human $\alpha_{1C}$ adrenoceptor at least ten-fold more than it activates a human dopamine $D_1$, $D_2$, $D_3$, or $D_5$ receptor.

The invention also provides that the $\alpha_{1C}$ selective agonist used to practice the method of treating urinary incontinence activates the human $\alpha_{1C}$ adrenoceptor at least ten-fold more than it activates a human serotonin $5\text{-}HT_{1A}$, $5\text{-}HT_{1D\alpha}$, $5\text{-}HT_{1D\beta}$, $5\text{-}HT_{1E}$, $5\text{-}HT_{1F}$, $5\text{-}HT_2$, or $5\text{-}HT_7$ receptor.

The present invention further provides a method of inducing contraction of urethra and bladder neck tissues which comprises contacting the urethra and bladder neck tissues with an effective contraction-inducing amount of an $\alpha_{1C}$ selective agonist which activates a human $\alpha_{1C}$ adrenoceptor at least ten-fold more than it activates a human $\alpha_{1A}$ adrenoceptor and a human $\alpha_{1B}$ adrenoceptor.

The invention further provides a method of inducing contraction of urethra and bladder neck tissues which comprises contacting the urethra and bladder neck tissues with an effective contraction-inducing amount of an $\alpha_{1C}$ selective agonist which activates a human $\alpha_{1C}$ adrenoceptor at least 50-fold more than it activates a human $\alpha_{1A}$ adrenoceptor and a human $\alpha_{1B}$ adrenoceptor.

The invention provides a method of inducing contraction of urethra and bladder neck tissues which comprises contacting the urethra and bladder neck tissues with an effective contraction-inducing amount of an $\alpha_{1C}$ selective agonist which activates a human $\alpha_{1C}$ adrenoceptor at least 100-fold more than it activates a human $\alpha_{1A}$ adrenoceptor and a human $\alpha_{1B}$ adrenoceptor.

The invention also provides a method of inducing contraction of urethra and bladder neck tissues which comprises contacting the urethra and bladder neck tissues with an effective contraction-inducing amount of an $\alpha_{1C}$ selective agonist which activates a human $\alpha_{1C}$ adrenoceptor at least 200-fold more than it activates a human $\alpha_{1A}$ adrenoceptor and a human $\alpha_{1B}$ adrenoceptor.

The $\alpha_{1C}$ selective agonist used to practice the method of inducing contraction of urethra and bladder neck tissues further has the characteristic that it does not antagonize a human $\alpha_{1A}$ adrenoceptor and a human $\alpha_{1B}$ adrenoceptor.

Desirably, the $\alpha_{1C}$ selective agonist used to practice the method of inducing contraction of urethra and bladder neck tissues activates the human $\alpha_{1C}$ adrenoceptor at least ten-fold more than it activates any human $\alpha_2$ adrenoceptor and any β adrenoceptor. Some examples of $\alpha_2$ adrenoceptors include the $\alpha_{2A}$, $\alpha_{2B}$, and $\alpha_{2C}$ receptors The invention also provides that the $\alpha_{1C}$ selective agonist used to practice the method of inducing contraction of urethra and bladder neck tissues further has the characteristic that it does not antagonize any human $\alpha_2$ adrenoceptor and any β adrenoceptor. Some examples of $\alpha_2$ adrenoceptors include the $\alpha_{2A}$, $\alpha_{2B}$, and $\alpha_{2C}$ receptors Desirably, the $\alpha_{1C}$ selective agonist used to practice the method of inducing contraction of urethra and bladder neck tissues activates the human $\alpha_{1C}$ adrenoceptor at least ten-fold more than it activates a human histamine $H_1$ or $H_2$ receptor.

The invention further provides that the $\alpha_{1C}$ selective agonist used to practice the method of inducing contraction of urethra and bladder neck tissues activates the human $\alpha_{1C}$ adrenoceptor at least ten-fold more than it activates a human dopamine $D_1$, $D_2$, $D_3$, or $D_5$ receptor.

The invention also provides that the c selective agonist used to practice the method of inducing contraction of urethra and bladder neck tissues activates the human $\alpha_{1C}$ adrenoceptor at least ten-fold more than it activates a human serotonin $5\text{-}HT_{1A}$, $5\text{-}HT_{1D\alpha}$, $5\text{-}HT_{1D\beta}$, $5\text{-}HT_{1E}$, $5\text{-}HT_{1F}$, $5\text{-}HT_2$, or $5\text{-}HT_7$ receptor.

In one embodiment the invention provides a method of treating urinary incontinence which comprises administering to the subject a therapeutically effective amount of a compound having the structure:

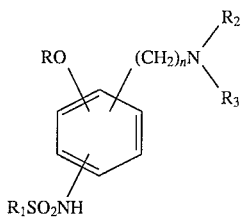

where n is an integer from 1 to 6; R is H or $C_1$–$C_6$ alkyl; $R_1$ is $C_1$–$C_6$ alkyl, phenyl, naphthyl, substituted phenyl or naphthyl where the substituent is a halogen, or a $C_1$–$C_6$ alkyl or alkoxy group; where

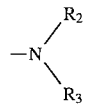

is an amino group or a heterocyclic group; the heterocyclic group is piperidine, morpholine, piperazine, pyrrolidine, hexamethylene, or thiomorpholine, the heterocyclic group being bonded through the nitrogen atom thereof to the $(CH_2)_n$ group; the amino group, where $R_2$ is H, $C_1$–$C_6$ alkyl, benzyl, or benzyhydryl and where $R_3$ is H; $C_1$–$C_{10}$ alkyl; $C_2$–$C_{10}$ alkenyl; $C_3$–$C_{10}$ cycloalkyl or cycloalkenyl.

The present invention also provides that the compound has the structure:

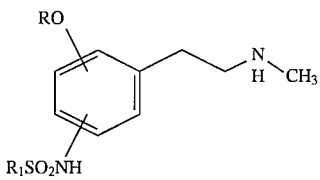

The invention further provides that the compound has the structure:

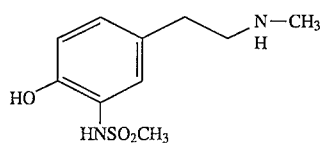

A further embodiment of the invention provides a method of treating urinary incontinence which comprises administering to the subject a therapeutically effective amount of a compound having the structure:

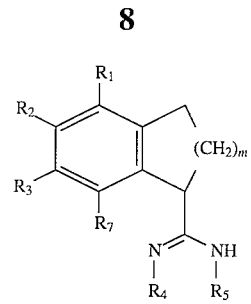

where m is an integer from 0 to 2; where each of $R_1$, $R_2$, $R_3$ and $R_7$ is independently H; OH; $C_1$–$C_6$ alkyl or alkoxy; halo; amino; acetamido or $NHSO_2R$ with R being H or $C_1$–$C_6$ alkyl; where $R_1$ and $R_2$ or $R_2$ and $R_3$ or $R_3$ and $R_7$ taken together constitute a methylenedioxy, ethylenedioxy, benzimidazole or indole ring; where each of $R_4$ and $R_5$ are independently H or taken together has the following formula:

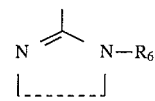

where the dashed line represents a single or double bond; and $R_6$ is H or $C_1$–$C_6$ alkyl; or a pharmaceutically acceptable salt thereof.

The invention also provides that the compound has the structure:

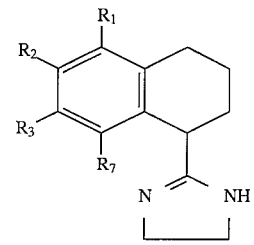

The invention further provides that the compound has the structure:

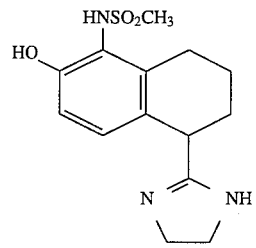

The invention also provides a method of treating urinary incontinence which comprises administering to the subject a therapeutically effective amount of a compound having the structure:

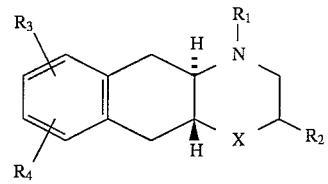

where each of $R_1$ and $R_2$ is independently H or $C_1$–$C_4$ alkyl; where $R_3$ is OH or $C_1$–$C_4$ alkoxy; and $R_4$ is $C_1$–$C_4$ alkylthio, alkylsulfoxide or alkylsulfone; Cl; Br; I or CF$_3$; where X is O, S, SO, SO$_2$, NH, NR$_1$ or NC(O)R$_1$; in free base or acid addition salt form.

The invention further provides that the compound has the structure:

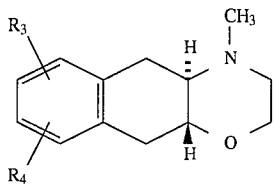

The invention specifically provides that the compound has the structure:

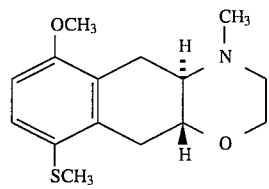

This invention is also directed to optical isomers of the compounds described above. The invention also provides for the (−) and (+) enantiomers of all compounds of the subject application described herein. Included in this invention are pharmaceutically acceptable salts and complexes of all of the compounds described herein. The salts include but are not limited to the following acids and bases. The following inorganic acids; hydrochloric acid, hydrofluoric acid, hydrobromic acid, hydroiodic acid, sulfuric acid and boric acid. The organic acids; acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid and mandelic acid. The following inorganic bases; ammonia, hydroxyethylamine and hydrazine. The following organic bases; methylamine, ethalamine, propylamine, dimethylamine, diethylamine, trimethylamine, triethylamine, ethylenediamine, hydroxyethylamine, morpholine, piperazine and guanidine. This invention further provides for the hydrates, isomorphs and polymorphs of all of the compounds described herein.

The present invention therefore provides a method of treating urinary incontinence, which comprises administering a quantity of any of the α$_{1C}$ receptor agonists defined herein in a quantity effective against urinary incontinence.

The drug may be administered to a patient afflicted with urinary incontinence by any conventional route of administration, including, but not limited to, intravenous, intramuscular, oral, subcutaneous, intratumoral, intradermal, and parenteral. The quantity effective against urinary incontinence is between 0.001 mg and 10.0 mg per kg of subject body weight. The method of treating urinary incontinence disclosed in the present invention may also be carried out using a pharmaceutical composition comprising any of the α$_{1C}$ receptor agonists as defined herein and a pharmaceutically acceptable carrier. The composition may contain between 0.05 mg and 500 mg of an α$_{1C}$ receptor agonist, and may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings. The drug may also be formulated as a transdermal patch.

Optimal dosages to be administered may be readily determined by those skilled in the art, and will vary with the particular α$_{1C}$ receptor agonist in use, the strength of the preparation, the mode of administration, and the advancement of the disease condition. Additional factors depending on the particular patient being treated will result in a need to adjust dosages, including patient age, weight, diet, and time of administration.

The term "therapeutically effective amount" as used herein refers to that amount of pharmaceutical agent that elicits in a tissue, system, animal or human, the biological or medicinal response that is being sought by a researcher, veterinarian, medical doctor or other clinician, which response includes alleviation of the symptoms of the disease being treated. The term "subject," as used herein refers to an animal, preferably a mammal, most preferably a human, who has been the object of treatment, observation or experiment.

The binding and functional properties of compounds at the different human receptors were determined in vitro using cultured cell lines that selectively express the receptor of interest. These cell lines were prepared by transfecting the cloned cDNA or cloned genomic DNA or constructs containing both genomic DNA and cDNA encoding the human α-adrenoceptors as further described in detail in Example 10 hereinbelow. In connection with this invention, a number of cloned human receptors discussed herein, either as plasmids or as stably transfected cell lines, have been made pursuant to, and in satisfaction of, the Budapest Treaty on the International Recognition of the Deposit of Microorganisms for the Purpose of Patent Procedure, and are made with the American Type Culture Collection, 12301 Parklawn Drive, Rockville, Md. 20852. Specifically, these deposits have been accorded ATCC Accession Numbers as follows in Table 1:

TABLE 1

| | ATCC Deposits: | | |
|---|---|---|---|
| Designation | Receptor | ATCC Accession No. | Date of Deposit |
| | Cell lines: | | |
| L-α$_{1A}$ | human α$_{1A}$ | CRL 11138 | 09/25/1992 |
| L-α$_{1B}$ | human α$_{1B}$ | CRL 11139 | 09/25/1992 |
| L-α$_{1C}$ | human α$_{1C}$ | CRL 11140 | 09/25/1992 |
| L-α$_{2A}$ | human α$_{2A}$ | CRL 11180 | 11/6/1992 |
| L-NGC-α$_{2B}$ | human α$_{2B}$ | CRL 10275 | 10/25/1989 |
| Y-a2B-2 | human α$_{2B}$ | CRL 11888 | 05/11/1995 |
| L-α$_{2C}$ | human α$_{2C}$ | CRL 11181 | 11/6/1992 |
| Ltk-8-30-84 | human 5-HT$_{1D1}$ | CRL 10421 | 04/17/1990 |
| Ltk-11 | human 5-HT$_{1D2}$ | CRL 10422 | 04/17/1990 |
| 5HT$_{1E}$-7 | human 5-HT$_{1E}$ | CRL 10913 | 11/6/1991 |
| L-5-HT$_{1F}$ | human 5-HT$_{1F}$ | CRL 10957 | 12/27/1991 |
| L-5HT-4B | human 5-HT$_{4B}$ | CRL 11166 | 10/20/1992 |
| 5HT1A-3 | human 5-HT$_{1A}$ | CRL 11889 | 05/11/1995 |
| L-NGC-5HT$_2$ | human 5-HT$_2$ | CRL 10287 | 10/31/1989 |
| | Plasmids: | | |
| pcEXV-D2 | human D2 | 75344 | 11/6/1992 |
| pcEXV-H2 | human H2 | 75345 | 11/6/1992 |
| pcEXV-H1 | human H1 | 75346 | 11/6/1992 |

Cell Transfections

Transient transfections of COS-7 cells with various plasmids were performed using the DEAE-Dextran method, which is well-known to those skilled in the art. Briefly, a plasmid comprising an expression vector for the receptor of interest was added to monolayers of COS-7 cells bathed in a DEAE-Dextran solution. In order to enhance the efficiency of transfection, dimethyl sulfoxide was typically also added, according to the method of Lopata (Lopata, et al., 1984). Cells were then grown under controlled conditions and used in experiments after about 72 hours.

Stable cell lines were obtained using means which are well-known in the art. For example, a suitable host cell was typically cotransfected, using the calcium phosphate technique, with a plasmid comprising an expression vector for the receptor of interest and a plasmid comprising a gene which allows selection of successfully transfected cells. Cells were then grown in a controlled environment, and selected for expression of the receptor in interest. By continuing to grow and select cells, stable cell lines were obtained expressing the receptors described and used herein.

Binding Assays

The binding of a test compound to a receptor of interest was generally evaluated by competitive binding assays using membrane preparations derived from cells which expressed the receptor. First, conditions were determined which allowed measurement of the specific binding of a compound known to bind to the receptor. Then, the binding of the known compound to the receptor in membrane preparations was evaluated in the presence of several different concentrations of the test compound. Binding of the test compound to the receptor resulted in a reduction in the amount of the known compound which was abound to the receptor. A test compound having a high affinity for the receptor of interest would displace a given fraction of the bound known compound at a concentration lower than the concentration which would be required if the test compound had a low affinity for the receptor of interest.

The data shown in the Table 2 indicate that it is the $\alpha_{1C}$-adrenoceptor which is responsible for mediating the contractile response to adrenoceptor agonists in the urethra of mammals, particularly humans. This in vitro property is recognized in the art as correlating with efficacy in treating urinary incontinence in vivo.

This invention will be better understood from the Experimental Details which follow. However, one skilled in the art will readily appreciate that the specific methods and results discussed are merely illustrative of the invention as described more fully in the claims which follow thereafter.

Experimental Details

Phenylephrine, prazosin, 5-methylurapidil, and BMY 7378 were obtained from Research Biochemicals, Inc. Other compounds were prepared according to the examples which follow.

EXAMPLE 1

Synthesis of (±)-N-[5-(4,5-Dihydro-1H-imidazol-2-yl)-2-hydroxy-5, 6, 7, 8-tetra-hydronaphthalen-1-yl] methanesulfonamide (A-61603) 5-Nitro-6-methoxy-1-tetralone.

To a solution of 100 ml of 70% $HNO_3$ was added 6-methoxytetralone (Aldrich Chemical Co., Milwaukee, Wis., 4.0 g, 23 mmol) over 1 h period at 0° C. The resulting solution was stirred for 24 h at 25° C. The reaction mixture was then poured into water to yield a yellow precipitate, which was subjected to column chromatography (40% EtOAc-Hexane) to yield 2.2 g (43%) of the desired product. $^1$H NMR (300 MHz, $CDCl_3$): δ 2.12 (qt, 2H, J=6.9 Hz), 2.61 (t, 2H, J=6.9 Hz), 2.83 (t, 2H, J=6.9 Hz), 3.93 (s, 3H), 6.98 (d, 1H, J=8.9 Hz), 8.14 (d, 1H, J=8.9 Hz).

Synthesis of (±)-6-Methoxy-5-nitro-1-trimethylsilyloxy-1,2,3,4-tetrahydronaphthalene-1-carbonitrile.

To a solution of 5-nitro-6-methoxy-1-tetralone (0.93 g, 4.2 mmol) in 20 ml of $CH_2Cl_2$ was added $ZnI_2$ (100 mg, 0.31 mmol) and TMSCN (0.84 ml, 6.3 mmol) and the resulting solution was stirred for 2 h at 25° C. The reaction mixture was concentrated in vacuo to provide the desired product as a colorless oil, which was used in the next step without purification. $^1$H NMR (300 MHz, $CDCl_3$): δ 0.028 (s, 9H), 1.88–2.35 (m, 4H), 2.67 (t, 2H, J=6.1 Hz), 3.88 (s, 3H), 6.97 (d, 1H, J=8.9 Hz), 7.71 (d, 1H, J=8.9 Hz).

Synthesis of (±)-6-Methoxy-5-nitro-3,4-dihydronaphthalene-1-carbonitrile.

A solution of 6-methoxy-5-nitro-1-trimethylsilyloxy-1,2,3,4-tetrahydronaphthalene-1-carbonitrile (1.3 g, 4.0 mmol) and AcCl (1.0 ml) in 20 ml AcOH was stirred for 2 h at 80°–100° C. The resulting reaction mixture was concentrated in vacuo to yield the desired product as a colorless oil (0.86 g, 4.0 mmol, 96% for two steps), which was subjected to the following step without any further purification. $^1$H NMR (300 MHz, $CDCl_3$): δ 2.48 (dt, 2H, J=2.3, 6.7 Hz), 2.78 (t, 2H, J=8.9 Hz), 3.89 (s, 3H), 6.82 (t, 1H, J=2.3 Hz), 6.92 (d, 1H, J=8.9 Hz), 7.53 (d, 1H, J=8.9 Hz).

Synthesis of (±)-6-Methoxy-5-nitro-1,2,3, 4-tetrahydronaphthalene-1-carbonitrile.

To a solution of 6-methoxy-5-nitro-3,4-dihydronaphthalene-1-carbonitrile (0.41 g, 1.8 mmol) in 10 ml of EtOH was added $NaBH_4$ (0.20 g, 5.3 mmol) and the resulting reaction mixture was stirred for 30 min at 25° C. The solvent was removed in vacuo to yield an oily residue which was dissolved in EtOAc and washed with brine. The organic layer was dried over $Na_2SO_4$ and concentrated in vacuo to yield the desired product as a colorless oil (0.42 g, >95%) which was subjected to a following reaction without purification. $^1$H NMR (300 MHz, $CDCl_3$): δ 1.86 (m, 2H), 2.04 (m, 2H), 2.62 (q, 2H, J=6.3 Hz), 3.83 (s, 3H), 4.17 (t, 1H, J=6.3 Hz), 7.10 (d, 1H, J=8.9 Hz), 7.45 (d, 2H, J=8.9 Hz).

Synthesis of (±)-6-Methoxy-5-amino-1,2,3, 4-tetrahydronaphthalen-1-carbonitrile.

A solution of 6-methoxy-5-nitro-1,2,3,4-tetrahydronaphthalene-1-carbonitrile (0.42 g, 1.8 mmol) and catalytic amount of 10% Pd/C in 100 ml of MeOH was stirred under $H_2$ for 12 h at 25° C. The reaction mixture was filtered and concentrated in vacuo to yield the desired product as a colorless oil (0.36 g, >95%). $^1$H NMR (300 MHz, $CDCl_3$): δ 1.93 (m, 4H), 2.48 (qt, 2H, J=5.7 Hz), 3.79 (s, 3H), 3.99 (t, 1H, J=6.3 Hz), 6.68 (dd, 2H, J=8.0, 8.9 Hz).

Synthesis of (±)-N-(5-Cyano-2-methoxy-5,6,7,8-tetrahydronaphthalen-1-yl) methane-sulfonamide.

To a solution of 6-methoxy-5-amino-1, 2,3,4-tetrahydronaphthalene-1-carbonitrile (1.7 g, 8.3 mmol) in 20 ml of anhydrous pyridine was added methanesulfonyl chloride (1.9 ml, 1.2 mmol). The resulting solution was stirred for 2 h at 25° C. The reaction mixture was concentrated in vacuo to yield an oily residue which was redissolved in EtOAc and washed with aqueous NaHCO$_3$. The organic layer was dried over Na$_2$SO$_4$ and concentrated in vacuo to provide an oily residue which was purified by column chromatography (EtOAc, neat) to yield 1.5 g (65%) of the desired product. $^1$H NMR (300 MHz, CDCl$_3$): δ 6 1.82 (m, 1H), 1.94 (m, 1H), 2.14 (m, 2H), 2.96 (s, 3H), 3.03 (q, 2H, J=8.8 Hz), 3.84 (s, 3H), 3.96 (t, 1H, J=6.3 Hz), 6.85 (d, 1H, J=8.9 Hz), 7.39 (d, 1H, J=8.9 Hz).

Synthesis of (±)-N-[5-(4,5-Dihydro-1H-imidazol-2-yl)-2 -methoxy-5,6,7,8-tetra-hydronaphthalen-1-yl] methanesulfonamide.

N-(5-Cyano-2-methoxy-5,6,7,8-tetrahydronaphthalen-1-yl)methane-sulfonamide (1.5 g, 5.4 mmol) was dissolved in 200 ml of MeOH and cooled to 0° C. The solution was then treated with dry HCl gas for 2 h, sealed tightly and stored for 12 h at 25° C. The solvent was removed and the residue was redissolved in 100 ml of MeOH, followed by addition of ethylenediamine (0.67 ml, 10 mmol). The resulting solution was stirred at reflux for 12 h. The reaction mixture was concentrated in vacuo, yielding an oily residue which was subjected to column chromatography (25% NH$_3$ sat'd MeOH-CHCl$_3$) to provide 1.3 g (76%) of the desired product. $^1$H NMR (300 MHz, CD$_3$OD): δ 1.78 (m, 2H), 1.96 (m, 1H), 2.12 (m, 1H), 2.95 (broad t, 2H), 2.98 (s, 3H), 3.82 (s, 3H), 3.90 (broad s, 4H), 4.11 (t, 1H, J=6.3 Hz), 6.96 (t, 1H, J=8.9 Hz), 7.05 (t, 1H, J=8.9 Hz).

Synthesis of (±)-N-[5-(4,5-Dihydro-1H-imidazol-2-yl) -2 -hydroxy-5, 6, 7, 8-tetra-hydronaphthalen-1-yl]methanesulfonamide (A-61603).

To a solution of N-[5-(4,5-dihydro-1H-imidazol-2-yl)-2-methoxy-5,6,7,8-tetra-hydronaphthalen-1-yl]methane-sulfonamide (0.3 g, 0.9 mmol) in 100 ml of CHCl$_3$ was added BBr$_3$ (2.0 ml, 2.0 mmol) at −78° C. The resulting reaction mixture was stirred for 12 h at 25° C. The reaction mixture was then recooled to −78° C. and 2 ml of MeOH was added. The reaction mixture was warmed to 25° C. and stirred for another 3 h. It was then concentrated in vacuo to provide a light yellow solid (0.35 g, >95%) which was identified as the HBr salt of the desired product, mp 263–265 ° C. $^1$H NMR (300 MHz, CD$_3$OD): δ 1.78 (m, 2H), 1.90 (m, 1H), 2.04 (m, 1H), 2.93 (broad t, 2H), 3.05 (s, 3H), 3.86 (s, 4H), 4.06 (t, 1H, J=6.3 Hz), 6.79 (d, 1H, J=8.9 Hz), 6.92 (d, 1H, J=8.9 Hz), 9.58 (s, 1H); Anal. Cal. For C$_{14}$H$_{19}$N$_3$O$_3$S. 1.0HBr requires C, 43.7; H, 5.12; N, 10.7. Found: C, 42.8; H, 4.95; N, 10.3.

EXAMPLE 2

Synthesis of N-[2-Hydroxy-5-[2-methylamino) ethyl]phenyl]-methanesulfonamide (SK&F 102652)4-Hydroxy-N-methyl-3-nitrobenzeneacetamide.

A mixture of 5 g (25.38 mmol) of 3-nitro-4-hydroxyphenylacetic acid (from Aldrich Chemical Co., Milwaukee, Wis.) in 20 mL of thionyl chloride was heated at reflux for 45 min. The reaction mixture was cooled and poured into 80 mL of hexane. The resulting precipitate was collected by filtration, washed with hexane, and air-dried to yield a yellow solid. A solution of this acid chloride in 100 mL of dichloromethane was cooled in an ice bath and stirred while excess methylamine was distilled in dropwise. The mixture was stirred at room temperature overnight. The precipitated solid was collected by filtration and dissolved in water. It was acidified to pH 2 with 3 N HCl and extracted with dichloromethane to yield a yellow solid 4.2 g(80%). The title compound was used in the next step without further purification. $^1$H NMR (300 MHz, CDCl$_3$) δ 10.50 (s, 1H), 7.97 (s, 1H), 7.50 (d, 1H, J=9.0 Hz), 7.11 (d, 1H, J=9.0 Hz), 5.4 (brs, 1H), 3.49 (s, 2H), 2.78 (d, 3H, J=6.0 Hz).

Synthesis of 4-Methoxy-N-methyl-3-nitrobenzeneacetamide.

To a solution of 4.2 g (19.8 mmol) of 4-hydroxy-N-methyl-3 -nitrobenzeneacetamide in 50 mL of DMF containing 5.5 g of anhydrous potassium carbonate was added 5.6 mL of dimethyl sulfate. The mixture was heated at 60°–70° C. for 45 min, treated with an additional 3.0 mL of methyl sulfate, and heated for another 30 min. The mixture was cooled, poured into 200 mL water, and extracted with dichloromethane. The extracts were washed with water, dried and evaporated to give a solid which was recrystallized from ethanol-water to afford 3.7 g of a yellowish solid (82%). $^1$H NMR (300 MHz, CDCl$_3$) δ 7.71 (s, 1H), 7.47 (d, 1H, J =9.0 Hz), 7.25 (d, 1H, J =8.4 Hz), 5.71 (brs, 1H), 3.90 (s, 3H) 3.47 (s, 2H), 2.75 (d, 3H, J=4.8 Hz).

Synthesis of 4-Methoxy-N-methyl-3-[(methylsulfonyl)amino]-benzeneacetamide.

A solution of 3.6 g (16.3 mmol) of 4-methoxy-N-methyl-3-nitrobenzeneacetamide was hydrogenated using hydrogen gas at 50 psi in 40 mL of ethanol over 200 mg of Pd/C (10%) for 6 h. The catalyst was removed by filtration and solvent was evaporated to give 2.9 g of white solid. This solid was dissolved in 30 mL of pyridine and treated dropwise with 1.5 mL (19.4 mmol) of methanesulfonyl chloride in 5 mL of pyridine. The reaction mixture was warmed to 65° C. for 30 min and then stirred at room temperature overnight. The pyridine was evaporated and the residue taken up in 40 mL of water, adjusted to pH 6.7, and cooled in an ice bath. The resulting precipitate was removed by filtration and dried to give 1.7 g of an off-white solid (42%). Recrystallization from methanol gave white crystals. $^1$H NMR (300 MHz, CDCl$_3$) δ 7.35 (s, 1H), 7.04 (d, 1H, J=9.0 Hz), 6.85 (d, 1H, J=8.4 Hz),6.78 (brs, 1H),5.41 (brs, 1H), 3.85 (s, 3H) 3.46 (s, 2H), 2.94 (s, 3H), 2.73 (d, 3H, J=4.8 Hz).

Synthesis of N-[2-Methoxy-5-[2-methylamino) ethyl]phenyl]-methanesulfonamide.

A solution of 0.8 g (2.89 mmol) of 4-methoxy-N-methyl-3-[(methylsulfonyl) amino]-benzeneacetamide in 20 ml of dry THF was stirred and cooled in ice as a 1 M solution of borane in THF (15 mL) was added dropwise. After the addition was complete, the mixture was warmed to 65° C. for 6 h. It was cooled and treated with 25 mL of methanol, followed by 1 mL of 6 N HCl. The mixture was evaporated to yield a white residue which was dissolved in a minimum amount of hot methanol, filtered, and treated with ethyl acetate until cloudy and allowed to crystallize. The solid was removed by filtration and dried to give 0.54 g of white crystals (72%). $^1$H NMR (300 MHz, CD$_3$OD) δ 7.28 (s, 1H), 7.07 (d, 1H, J=9.0 Hz), 7.00 (d, 1H, J=8.4 Hz), 3.83 (s, 3H) 3.19–3.14 (m, 2H),2.90–2.85(m, 2H), 2.86 (s, 3H) 2.66 (s, 3H,).

Synthesis of N-[2-Hydroxy-5-[2-methylamino)ethyl]phenyl]-methanesulfonamide (SK&F 102652).

A suspension of 0.2 g of N-[2-methoxy-5-[2-methylamino)ethyl]phenyl]-methanesulfonamide in 10 mL of dichloromethane in a dry ice-2-propanol bath was treated with 4 mL of 1 M $BBr_3$ in dichloromethane. It was allowed to warm to room temperature and stirred overnight. The mixture was treated with 50 mL of methanol, stirred for 1 h, evaporated, and treated again with methanol, and evaporated to dryness. This residue was taken up in minimum volume of hot methanol, treated with ethyl acetate, and allowed to crystallize to afford 0.17 g (67%) of tan crystals, mp 188°–189° C. $^1$H NMR (300 MHz, $CD_3OD$) δ 7.23 (s, 1H), 6.97 (d, 1H, J=9.0 Hz), 6.85 (d, 1H, J=8.4 Hz), 3.21–3.16 (m, 2H), 2.92 (s, 3H) 2.90–2.84 (m, 2H), 2.68 (s, 3H,). Anal. Calcd for $C_{10}H_{17}BrN_2O_3S0.0.05$ $CH_2Cl_2$: C, 36.69; H, 5.23; N, 8.50. Found: C, 36.57; H, 5.14; N, 8.26.

EXAMPLE 3

Synthesis of (±)-4-Methyl-6-methoxy-9-thiomethoxy-3,4,4a,5,10,10a-hexahydro-2H-naphtho[2,3-b][1,4]-oxazine (SDZ NVI 085)1,4 Dihydro-5-methoxynaphthalene.

To a refluxing solution of 1-methoxynaphthalene (Aldrich Chemical Co., Milwaukee, Wis., 5.5 g, 34 mmol) in 80 ml of EtOH was added sodium (5.7 g, 250 mmol) in pieces under Ar. When all of the sodium was consumed, the reaction was cooled to 25° C. and stirred for additional 3 h. The reaction mixture was carefully quenched by adding 100 ml of water and extracted with EtOAc. The organic layer was dried over $Na_2SO_4$ and concentrated in vacuo to yield an oily residue which was purified by column chromatography (30% EtOAc-Hexane) to yield 2.8 g (52%) of the desired product as a colorless oil. $^1$H NMR (300 MHz, $CDCl_3$): δ 3.27(m, 2H), 3.39 (m, 2H), 3.82 (s, 3H), 5.85 (m, 2H), 6.67–6.75 (m, 2H), 7.13 (t, 1H, J=7.9 Hz).

Synthesis of (±)-6-Methoxy-1a,2,7,7a-tetrahydro-1-oxacyclopropan[b]naphthalene.

To a solution of 1,4 dihydro-5-methoxynaphthalene (2.8 g, 17.5 mmol) in 50 ml of $CH_2Cl_2$ was added MCPBA (8.5 g, 50 mmol) in one portion. The resulting solution was stirred for 3 h at 0° C. The reaction mixture was diluted with $CH_2Cl_2$ and poured into a mixture of ice (50 g) and $NaHCO_3$ sat'd aqueous solution (150 ml ). The organic layer was separated and the aqueous layer was extracted with $CH_2Cl_2$. The combined organic layers were washed with aqueous $NaHCO_3$, dried over $MgSO4$ and concentrated in vacuo to yield an oil which was subjected to column chromatography ($CH_2Cl_2$, neat) to yield 1.7 g (59%) of the desired product as a colorless oil. $^1$H NMR (300 MHz, $CDCl_3$): δ 2.78 (d, 1H, J=18.2 Hz), 3.21(AB q, 2H, J=18.3 Hz), 3.47 (m, 3H), 3.77 (s, 3H), 6.66(m, 2H), 7.08 (t, 1H, J=7.8 Hz).

Synthesis of (±)-3-Azido-5-methoxy-1,2,3,4-tetrahydronaphthalen-2-ol.

To a solution of 6-methoxy-1a, 2,7,7a-tetrahydro-1-oxacyclo-propan [b]naphthalene (1.7 g, 9.7 mmol) in 20 ml of DMSO was added sodium azide (5.6 g, 86 mmol) and $H_2SO_4$ (0.2 ml). The resulting suspension was stirred for 17 h at 25° C. The reaction mixture was diluted with EtOAc and washed with brine. The organic layer was dried over $MgSO_4$ and concentrated in vacuo, yielding an oil which was subjected to column chromatography (EtOAc, neat) to provide 1.9 g (89%) of a mixture of two regioisomers in a 1:1 ratio. Two isomers were separated by fractional recrystallization in hexane to provide 0.6 g of the desired product, mp 83°–84° C. $^1$H NMR (300 MHz, $CDCl_3$ ): δ 1.61 (s, 1H), 2.60 (dd, 1H, J=10.6, 17.0 Hz), 2.84 (dd, 1H, J=10.1, 15.9 Hz), 3.19 (dd, 1H, J=5.3, 15.9 Hz), 3.37 (dd, 1H, J=5.8, 17.0 Hz), 3.70 (m, 1H), 3.84 (s, 3H), 3.88 (m, 1H), 6.70(m, 2H), 7.17 (t, 1H, J=7.8 Hz).

Synthesis of (±)-3-Amino-5-methoxy-1, 2,3,4 -tetrahydronaphthalen-2-ol.

A solution of 3-azido-5 -methoxy-1,2,3,4-tetrahydronaphthalen-2-ol (1.8 g, 8.0 mmol) in 150 ml of MeOH was stirred with 10% Pd/C (20 mg) under $H_2$ (18 psi) for 4 h. The reaction mixture was filtered and concentrated in vacuo to provide 1.4 g (91%) of the desired product as a colorless oil which was used in the next reaction without purification. $^1$H NMR (300 MHz, $CDCl_3$ ): δ 2.0 (broad s, 2H), 2.24 (dd, 1H, J=10.4, 16.8 Hz), 2.84 (m, 2H), 3.16 (m, 2H), 3.59 (m, 1H), 3.78 (s, 3H), 6.66 (m, 2H), 7.09 (t, 1H, J=7.9 Hz).

Synthesis of (±)-6-Methoxy-4a, 5,10,10a-tetrahydro-4H-naphtho[2,3-b][1,4]oxazin-3-one.

To a solution of 3-amino-5-methoxy-1,2,3,4-tetrahydronaphthalen-2-ol (1.7 g, 8.8 mmol) and triethylamine (1.5 ml, 11 mmol) in 100 ml of $CH_2Cl_2$ was added chloroacetyl chloride (1.0 g, 8.9 mmol) in 10 ml of $CH_2Cl_2$ dropwise at 0° C. The resulting solution was stirred for 1.5 h at 25° C. The reaction mixture was then diluted with EtOAc and washed with 1N aqueous HCl. Organic layer was dried over $Na_2SO_4$ and concentrated in vacuo, yielding an oil which corresponds to the amide. The oily residue was redissolved in 20 ml of THF, and NaH (0.35 g, 8.8 mmol) and tetrabutylammonium iodide (0.25 g, 0.67 mmol) were added into the solution at 0° C. The reaction mixture was stirred for 12 h at 25 ° C. It was diluted with EtOAc and washed with brine. The organic layer was dried over $Na_2SO_4$ and concentrated in vacuo, yielding an oily residue which was purified by column chromatography (50% $CH_2Cl_2$-EtOAc) to provide 1.4 g (68%) of the desired product. $^1$H NMR (300 MHz, $CDCl_3$): δ 2.45 (dd, 1H, J=10.5, 16.7 Hz), 2.85 (m, 1H), 3.11–3.34 (m, 2H), 3.65(m, 2H), 3.79 (s, 3H), 4.28 (AB q, 2H, 16.7 Hz), 6.68 (m, 2H), 7.07 (t, 1H, J=7.9 Hz).

Synthesis of (±)-6-Methoxy-3,4,4a,5,10,10a-hexahydro-2H-naphtho[2,3-b][1,4]oxazine.

To a solution of 6-methoxy-4a,5,10,10a-tetrahydro-4H-naphto[2,3-b][1,4]oxazin-3-one (1.4 g, 6.0 mmol) in 100 ml of THF was added 10 ml of $LiAlH_4$ solution in THF (10 mmol). The resulting solution was stirred for 2 h at reflux. The reaction was quenched with ice and the reaction mixture was then diluted with EtOAc. Filtration of the reaction mixture provided a clean organic layer which was concentrated in vacuo to yield 1.2 g (92%) of the desired product as a colorless oil. $^1$H NMR (300 MHz, $CDCl_3$): δ 1.85 (s, 1H), 2.34 (dd, 1H, J=12.0, 17.0 Hz), 2.78–3.16 (m, 6H), 3.50 (ddd, 1H, J=5.2, 6.8, 10.5 Hz), 3.74 (m, 1H), 3.81 (s, 3H), 3.94 (m, 1H), 6.70 (m, 2H), 7.16 (t, 1H, J=7.6 Hz).

Synthesis of (±)-6-Methoxy-3,4,4a, 5,10,10a-hexahydro-2H-naphtho [2,3-b][1,4]oxazine-4-carboxylic acid benzyl ester.

To a solution of 6-methoxy-3,4,4a,5,10,10 a-hexahydro-2H-naphtho-[2,3-b][1,4]oxazine (0.62 g, 2.7 mmol) in 10 ml of $CH_2Cl_2$ was added triethylamine (1.0 ml, 7.2 mmol ) and benzyl chloroformate (0.6 ml, 4.1 mmol). The resulting mixture was stirred at 25° C. for 3 h. It was then diluted with 100 ml of EtOAc and washed with brine. The organic layer was dried over $Na_2SO_4$ and concentrated in vacuo, yielding an oily residue which was subjected to column chromatography (20% EtOAc-$CH_2Cl_2$) to provide 0.46 g (48%) of the desired product. $^1H$ NMR (300 MHz, $CDCl_3$): δ 2.45 (dd, 1H, J=10.6, 16.6 Hz), 2.83 (dd, 1H, J=10.3, 16.0 Hz), 3.04 (dd, 1H, J=5.0, 16.0 Hz), 3.68–3.88 (m, 6H), 3.76 (s, 3H), 4.02(m, 1H), 5.16 (AB q, 2H, J=17.6 Hz), 6.66 (m, 2H), 7.09 (t, 1H,J=7.8 Hz).

Synthesis of (±)-4-Methyl-6-methoxy-3,4,4a,5,10, 10a- hexahydro-2H-naphtho[2,3-b][1,4]oxazine.

To a solution of 6-methoxy-3,4,4a,5,10,10a-hexahydro-2H-naphtho-[2,3-b][1,4]oxazine-4-carboxylic acid benzyl ester (0.40 g, 1.1 mmol) in THF was added 2.8 ml of $LiAlH_4$ solution (1.0 M) in THF. The resulting solution was stirred at reflux for 3 h. The reaction mixture was quenched with ice, diluted with EtOAc and filtered through Celite. The organic layer was dried over $Na_2SO_4$ and concentrated in vacuo, yielding an oily residue which was subjected to column chromatography (5% MeOH-EtOAc) to yield 0.19 g (75%) of the desired product. $^1H$ NMR (300 MHz, $CDCl_3$): δ 2.07 (m, 1H), 2.28 (m, 1H), 2.37 (s, 3H), 2.49 (m, 1H), 2.77 (m, 2H), 2.97 (dd, 1H, J=5.5, 16.1 Hz), 3.28 (dd, 1H, J=5.5, 17.0 Hz), 3.55 (m, 1H), 3.79 (s, 3H), 3.86 (m, 2H), 6.67 (m, 2H), 7.09 (t, 1H, J=7.8 Hz).

Synthesis of (±)-4-Methyl-6-methoxy-9-iodo3,4,4a, 5,10,10a-hexahydro-2H-napto -[2,3-b][1,4]oxazine.

A solution of 4-methyl-6-methoxy-3,4,4a,5,10,10a-hexahydro-2H-naphtho[2,3-b][1,4]oxazine (0.37 g, 1.6 mmol) was dissolved in 7 ml of AcOH and heated to 50° C. To the solution of the amine was added a solution of $Hg(OAc)_2$ (0.62 g, 19 mmol) and $I_2$ (1.0 g, 3.8 mmol) in 30 ml of AcOH. The resulting solution was stirred for 1 h at 50° C. and 1.5 h at 25° C. The reaction mixture was filtered to remove mercury salts and concentrated in vacuo, yielding an oily residue which was subjected to column chromatography (5% $NH_3$ sat'd MeOH-EtOAc) to yield 0.25 g (44%) of the desired product. $^1H$ NMR (300 MHz, $CDCl_3$): δ 2.04 (m, 1H), 2.32 (dd, 1H, J=11.0, 18.0 Hz), 2.41 (s, 3H), 2.49 (m, 1H), 2.62 (dd, 1H, J=11.0, 17.0 Hz), 2.76 (m, 1H), 3.12 (dd, 1H, J=6.0, 17.0 Hz), 3.33 (dd, 1H, J=5.6, 17.0 Hz), 3.56 (m, 1H), 3,81 (s, 3H), 3.88 (m, 2H), 6.47 (d, 1H, J=7.8 Hz), 7.66 (d, 1H, J=7.8 Hz).

Synthesis of (±)-trans-4-Methyl-6-methoxy-9 -thiomethoxy-3,4,4a, 5,10,10a-hexahydro-2H-naphtho [2,3-b][1,4]oxazine (SDZ NVI 085).

To a suspension of $CH_3SLi$ (0.30 g, 5.5 mmol) in 6 ml of DMSO was added 4-methyl-6-methoxy-9 -iodo-3,4,4a, 5,10,10a-hexahydro-2H-naphtho-[2,3-b][1,4 ]oxazine (0.25 g, 0.7 mmol) and $Cu_2O$ (1.3 g, 9.1 mmol). The reaction mixture was stirred for 5 h at 80° C. It was diluted with EtOAc and washed with 4N $NH_4OH$ several times. The organic layer was dried over $Na_2SO_4$ and concentrated in vacuo to yield an oily residue which was subjected to column chromatography (5% MeOH-$CH_2Cl_2$) to yield 0.15 g (79%) of the desired product. $^1H$ NMR (300 MHz, $CDCl_3$): δ 2.09 (m, 1H), 2.32 (dd, 1H, J=10.5, 16.5 Hz), 2.39 (s, 3H), 2.41 (s, 3H), 2.45–2.80 (m, 3H), 3.27–3.40 (m, 2H), 3.60 (m, 1H), 3.82 (s, 3H), 3.90 (m, 2H), 6.72 (d, 1H, J=7.8 Hz), 7.14 (d, 1H, J=7.8 Hz). The product obtained was converted to the HCl salt and recrystallized from EtOAc-$Et_2O$ to obtain 0.17 g of the product as a white solid: mp 215°–217° C.; Anal. Cal. For $C_{15}H_{21}NO_2S.1.0HCl$ requires C, 56.9; H, 6.69; N, 4.43. Found: C, 56.5; H, 6.77; N, 4.38.

EXAMPLE 4

Synthesis of 1-(6,7-Dimethoxy-3,4-dihydro-1H-isoquinolin-2-yl)ethanone.

To a stirred solution of 6,7-dimethoxy-1,2, 3,4-tetrahydroisoquinoline (3.00 g, 15.4 mmol, 1.00 equiv) in anhydrous pyridine (100 mL) under argon at room temperature was added acetic anhydride (14.5 mL, 154 mmol, 10.0 equiv) over 15 min. The resulting mixture was stirred at room temperature for 2 h, and then at reflux for 6 h. The volatiles were removed by rotary evaporation at 80° C. under high vacuum. The residue was flash chromatographed on silica gel (MeOH-$CH_2Cl_2$ 8:92) to afford 3.21 g (89%) of viscous brown oil. The $^1H$ NMR spectrum reflected the presence of two slowly interconverting conformers in a ratio of 1.2 :1 at room temperature. $^1H$ NMR (300 MHz, $CDCl_3$) for conformer 1: δ 2.18 (s, 3 H), 2.83 (t, J=5.9 Hz, 2 H), 3.67 (t, J=5.9 Hz, 2 H), 3.86 (s, 3 H), 3.87 (s, 3 H), 4.66 (s, 2 H), 6.63 (s, 1 H), 6.65(s, 1 H). For conformer 2:δ 2.19 (s, 3 H), 2.77 (t, J=5.9 Hz, 2 H), 3.81 (t, J=5.9 Hz, 2 H), 3.86 (s, 3 H), 3.87 (s, 3 H), 4.56 (s, 2 H), 6.59 (s, 1 H), 6.63 (s, 1 H).

Synthesis of 2-[1-(6,7-Dimethoxy-3,4-dihydro-1 H-isoquinolin-2-yl) -ethylidineamino]-4,5-dimethoxybenzonitrile.

To a stirred solution of 1-(6,7-dimethoxy-3,4-dihydro-1H-isoquinolin-2-yl) ethanone (1.00 g, 4.25 mmol, 1.00 equiv) in $CHCl_3$ at room temperature under argon was added $POCl_3$ (143 μL, 1.53 mmol, 0.36 equiv). After 10 min, 2-amino-4,5-dimethoxybenzonitrile (763 mg, 4.28 mmol, 1.01 equiv) was added and the mixture was heated at reflux overnight. The mixture was cooled to room temperature and poured into 1 M aq. NaOH solution (50 mL), and the aqueous phase was extracted with $CH_2C_2$ (3×50 mL). The combined organic solutions were dried over $MgSO_4$ and concentrated. The residue was flash chromatographed on silica gel (MeOH-$CH_2Cl_2$ 5:95) to afford 482 mg (28%) of yellow solid: $^1H$ NMR (300 MHz, $CDCl_3$) δ 2.02 (s, 3 H), 2.87 (t, J=6.0 Hz, 2 H), 3.78 (t, J=6.0 Hz, 2 H), 3.85 (s, 6 H), 3.87 (s, 6 H), 4.70 (s, 2 H), 6.35 (s, 1 H), 6.65 (s, 2 H), 6.92 (s, 1 H); CIMS ($CH_4$) 424 $(M+C_2H_5)^+$, 396 $(M+H)^+$.

Synthesis of 2-(6,7-Dimethoxy-3,4-dihydro-1H-isoquinolin-2-yl)-6,7-dimethoxyquinolin-4-ylamine hemifumarate hydrate (abanoquil).

To a stirred solution of 2-[1-(6, 7-dimethoxy-3,4-dihydro-1H-isoquinolin-2-yl)-ethylidineamino]-4,5-dimethoxybenzonitrile (471 mg, 1.19 mmol, 1.00 equiv) in refluxing anhydrous N,N-dimethylacetamide (24 mL) under argon was added $ZnCl_2$ (339 mg, 2.49 mmol, 2.10 equiv) in three portions over 1 h. The solvent was removed by distillation at 70° C. under high vacuum. Ether (40 mL) was added to the residue, which was broken up with a stirring rod, and the mixture was stirred at 0° C. to precipitate the product. The supernatant was discarded, and the precipitate was washed twice more at 0° C. with ether. The solid residue was stirred with 1 M aq. NaOH (25 mL) and $CH_2C_2$ (25 mL) for 10 min, and the aqueous phase was extracted with $CH_2C_2$ (2×25 mL). The combined organic solutions were dried over $MgSO_4$ and concentrated to give 493 mg of brown oil, which was flash chromatographed on silica gel (MeOH-CH$_2$Cl$_2$ 12:88 followed by 2-propylamine-CH$_2$Cl$_2$ 5:95) to afford 151 mg (38%) of 2-(6,7-dimethoxy-3,4-dihydro-1H-isoquinolin-2-yl)-6,7-dimethoxyquinolin-4-ylamine as a tan solid: $^1$H NMR (300 MHz, CDCl$_3$) δ 2.90 (t, J=5.7 Hz, 2 H), 3.81 (t, J=5.7 Hz, 2 H), 3.86 (s, 3 H), 3.88 (s, 3 H), 3.93 (s, 3 H), 3.97 (s, 3 H), 4.64 (s, 2 H), 6.05 (s, 1 H), 6.66 (s, 1 H), 6.75 (s, 1 H), 7.02 (s, 1 H), 7.23 (s, 1 H); CIMS (CH$_4$) 424 (M+C$_2$H$_5$)$^+$, 396 (M+H)$^+$. To a solution of 2-(6,7-dimethoxy-3,4-dihydro-1H-isoquinolin-2-yl) -6,7-dimethoxyquinolin-4-ylamine (150 mg) in hot CH$_2$Cl$_2$ (4.5 mL) and MeOH (1.5 mL) was added a solution of fumaric acid (22.8 mg, 0.196 mmol, 0.50 equiv) in hot MeOH (3.0 mL). The resulting mixture was concentrated and the product was recrystallized from MeOH with hot filtration to afford, after filtration, 85 mg of light brown solid: m.p. 239°–240° C. Calcd. for C$_{22}$H$_{25}$N$_3$O$_4$·0.5C$_4$H$_4$O$_4$·0.75 H$_2$O: C, 61.73; H, 6.15; N, 9.00. Found: C,61.77; H, 6.17; N, 8.91.

EXAMPLE 5

Synthesis of (±)-2,6-Dimethyl-4-(4-nitrophenyl)-1,4-dihydro-pyridine-3,5-dicarboylicacid[3-(4,4-diphenyl piperidin-1-yl)propyl]ester methyl ester.

A solution of methyl 3-aminocrotonate (265 mg, 2.3 mmol, 1.0 equiv), 4-nitrobenzaldehyde (348 mg, 2.3 mmol, 01.0 equiv), and acetoacetic acid 3-[4,4-diphenylpiperidin-1-yl) propyl]ester (872 mg, 2.3 mmol, 1.0 equiv; Flockerzi, D.; Ulrich, W.-R. U.S. Pat. No. 4,975,440, 1990) in isopropanol was refluxed under argon with stirring for 68 hours. Cooling and removal of solvent gave a residue, which was purified by flash chromatography (SiO$_2$, EtOAc-hexane 1:1 and 2:1 followed by EtOAc) to afford 717 mg (51%) of yellow solid: $^1$H NMR (300 MHz, CDCl$_3$) δ 1.73 (m, 2 H), 2.22 (m, 2 H), 2.30–2.51 (m, 8 H), 2.34 (s, 3 H), 2.35 (s, 3 H), 3.63 (s, 3 H), 4.05 (dt, J=2.1, 7.9 Hz, 2 H), 5.06 (s, 1 H), 5.73 (br s, 1 H), 7.14 (m, 2 H), 7.27 (m, 8 H), 7.42 (dm, J=8.8 Hz, 2 H), 8.06 (dm, J=8.8 Hz, 2 H); $^{13}$C NMR (75 MHz, CDCl$_3$) δ 15.30, 19.65, 26.32, 36.11, 39.88, 44.60, 50.60, 51.12, 55.34, 62.66, 102.99, 107.55, 123.39, 125.67, 127.12, 128.33, 128.65, 144.80, 144.93, 146.36, 147.50, 154.78, 166.91, 167.43; IR (neat) 1698.0, 1684.7, 1517.5, 1345.7 cm$^{-1}$; CIMS (NH$_3$) 610 (M+1)$^+$, 553, 338.

Synthesis of (±)-2,6-Dimethyl-4-(4-nitrophenyl)-1,4-dihydro-pyridine-3,5-dicarboxylicacid [3-(4,4-diphenylpiperidin-1-yl) propyl]ester methyl ester hydrochloride (Compound 1).

To a solution of 2,6-dimethyl-4-(4-nitrophenyl) -1,4-dihydropyridine-3,5-dicarboxylicacid [3-(4,4-diphenyl -piperidin-1-yl) propyl]ester methyl ester (710 mg, 1.16 mmol, 1.0 equiv) in EtOH (5 mL) was added a solution of HCl in ether (1.0 M, 1.5 mL, 1.5 mmol, 1.3 equiv). The solvents were removed and the residue was dissolved in CH$_2$Cl$_2$. This solution was added dropwise to 25 mL of ether to afford, after filtration, 500 mg of yellow crystalline solid: m.p. 152°–153° C. Calcd. for C$_{36}$H$_{39}$N$_3$O$_6$ ·HCl: C, 66.92; H, 6.24; N, 6.50. Found: C, 66.70; H, 5.99; N, 6.27.

EXAMPLE 6

Synthesis of (±)-2-Amino-1-(2, 5 dimethoxyphenyl) ethanol (ST-1059) (2, 5, Dimethoxyphenyl)-hydroxy-acetonitrile.

To a solution of 4.0 g (24 mmol) of 2,5-dimethoxybenzaldehyde in 40 mL of dichloromethane containing 0.078 g(5% mmol) of KCN and 0.31 g (5% mmol) of 18-crown-6, was added trimethylsilylcyanide 2.62 g (26.4 mmol) dropwise. The reaction mixture was stirred at room temperature for 24 h. The reaction mixture was concentrated, dissolved in chloroform and washed with water, dried (sodium sulfate), concentrated in vacuo and purified by flash chromatography ( silica gel; hexane:ethyl acetate, 8:2) to afford 2.85 g (66%) of the desired compound as a yellow oil. $^1$H NMR (300MHz, CDCl$_3$) δ 6.95 (d, 1H, J=2.7 Hz), 6.85–6.84 (m, 2H), 5.52 (d, 1H, J=7.5 Hz), 3.93 (d, 1H, J=7.5 Hz), 3.83 (s, 3H), 3.73 (s, 3H)

Synthesis of (±)-2-Amino-1-(2, 5 dimethoxyphenyl) ethanol (ST-1059).

A solution of 2.84 g (14.7 mmol) of (2, 5 dimethoxyphenyl)-hydroxy acetonitrile in 10 ml of dry THF was stirred and cooled using ice bath as a 1 M solution of borane in THF (90 mL) was added dropwise. After the addition was complete, the mixture was heated at reflux for 20 h. It was cooled and treated with 40 mL of 6N hydrochloric acid and washed with ethyl acetate. The aqueous layer was neutralized with 1N sodium hydroxide and extracted with ethyl acetate and concentrated to afford the desired compound as a white solid 1.5 g (52%). $^1$H NMR (300MHz, CDCl$_3$) δ 6.97 (d, 1H, J=2.5 Hz), 6.73–6.69(m, 2H), 4.83–4.81(t, 1H, J=4.1 Hz), 3.72(s, 3H), 3.71(s, 3H), 2.89–2.65(m, 2H), 2.16(brs, 2H)

EXAMPLE 7

The binding and functional properties of compounds at the different human receptors were determined in vitro using cultured cell lines that selectively express the receptor of interest. These cell lines were prepared by transfecting the cloned cDNA or cloned genomic DNA or constructs containing both genomic DNA and cDNA encoding the human α-adrenoceptors as follows:

Human α$_{1A}$ Adrenoceptor

The entire coding region of the α1A receptor (1719 bp), including 150 basepairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequences were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid IA/EXJ (expression vector containing the α1A receptor gene) and the plasmid pGCcos3neo (plasmid containing the aminoglycoside transferase gene) into LM(tk$^-$), CHO, and NIH3T3 cells, using calcium phosphate technique. The cells were grown, in a controlled environment (37° C., 5% CO$_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 µg/ml streptomycin sulfate. Stable clones were then selected for resistance to the antibiotic G-418 (1 mg/ml), and membranes were harvested and assayed for their ability to bind [$^3$H] prazosin as described below (see "Radioligand Binding assays").

Human $\alpha_{1B}$ Adrenoceptor

The entire coding region of the α1B receptor (1563 bp), including 200 basepairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were obtained as described above.

Human $\alpha_{1C}$ Adrenoceptor

The entire coding region of the α1C receptor (1401 bp), including 400 basepairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6 Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were obtained as described above.

Radioligand Binding Assays.

Human $\alpha_1$-Adrenoceptors

Transfected cells from culture flasks were scraped into 5 ml of 5 mM Tris-HCl, 5 mM EDTA, pH 7.5, and lysed by sonication. The cell lysates were centrifuged at 1000 rpm. for 5 min at 4° C., and the supernatant was centrifuged at 30,000 ×g for 20 min at 4° C. The pellet was suspended in 50 mM Tris-HCl , 1 mM MgCl$_2$, and 0.1% ascorbic acid at pH 7.5. Binding of the α1 antagonist [$^3$H] prazosin (0.5 nM, specific activity: about 76.2 Ci/mmol) to membrane preparations of LM(tk-) cells was done in a final volume of 0.25 ml and incubated at 37° C. for 20 min. Nonspecific binding was defined as that binding which remained in the presence of 10 μM phentolamine(a concentration at least 100-fold greater than the affinity of phentolamine at any human adrenoceptors). The reaction was stopped by filtration through GF/B filters using a cell harvester. Equilibrium competition binding assays, routinely consisting of 7 different concentrations of the tested compounds, were analyzed using a non-linear regression curve-fitting computer program to obtain IC$_{50}$ values. The IC$_{50}$ values were converted to affinity constants (pK$_I$ ) by the method of Cheng and Prusoff (1973).

Human $\alpha_2$-Adrenoceptors

To determine the affinity of compounds at the α$_2$ receptors, LM(tk-) cell lines stably transfected with the genes encoding the α$_{2A}$, α$_{2B}$, and α$_{2C}$ receptors were used. Cell lysates were prepared as described above (see Radioligand Binding Assays), and suspended in 25 mM glycylglycine buffer (pH 7.6 at room temperature). Equilibrium competition binding assays were performed using [$^3$H] rauwolscine (0.5 nM), and nonspecific binding was determined by incubation with 10 μM phentolamine. The bound radioligand was separated by filtration through GF/B filters using a cell harvester.

Human Histamine H$_1$ Receptor

The coding sequence of the human histamine H$_1$ receptor, homologous to the bovine H$_1$ receptor, was obtained from a human hippocampal cDNA library, and was cloned into the eukaryotic expression vector pCEXV-3. The plasmid DNA for the H$_1$ receptor is designated pcEXV-H1, and was deposited on Nov. 6, 1992 under ATCC Accession No. 75346. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min. at 4° C. The pellet was suspended in 37.8 mM NaHPO$_4$, 12.2 mM KH$_2$PO$_4$, pH 7.5. The binding of the histamine H$_1$ antagonist [$^3$H] mepyramine (1 nM, specific activity: about 24.8 Ci/mM) was done in a final volume of 0.25 ml and incubated at room temperature for 60 min. Nonspecific binding was determined in the presence of 10 μM mepyramine. The bound radioligand was separated by filtration through GF/B filters using a cell harvester.

Human Histamine H$_2$ Receptor

The coding sequence of the human H$_2$ receptor was obtained from a human placenta genomic library, and cloned into the cloning site of PCEXV-3 eukaryotic expression vector. The plasmid DNA for the H$_2$ receptor is designated pcEXV-H2, and was deposited on Nov. 6, 1992 under ATCC Accession No. 75345. This construct was transfected into COS-7 cells by the DEAE-dextran method. Cells were harvested after 72 hours and lysed by sonication in 5 mM Tris-HCl, 5 mM EDTA, pH 7.5. The cell lysates were centrifuged at 1000 rpm for 5 min at 4° C., and the supernatant was centrifuged at 30,000×g for 20 min at 4° C. The pellet was suspended in 37.8 mM NaHPO$_4$, 12.2 mM K2PO$_4$, pH 7.5. The binding of the histamine H$_2$ antagonist [3H] tiotidine (5 nM, specific activity: about 70 Ci/mM) was done in a final volume of 0.25 ml and incubated at room temperature for 60 min. Nonspecific binding was determined in the presence of 10 μM histamine. The bound radioligand was separated by filtration through GF/B filters using a cell harvester.

Human Serotonin Receptors

5-HT$_{1D\alpha}$, 5-HT$_{1D\beta}$, 5-HT$_{1E}$, 5-HT$_{1F}$, and 5-HT$_7$ Receptors: The cell lysates of LM(tk-) clonal cell line stably transfected with the genes encoding each of these 5-HT receptor-subtypes were prepared as described above. The cell line for the 5-HT$_{1D\alpha}$receptor, designated as Ltk-8-30-84, was deposited on Apr. 17, 1990, and accorded ATCC Accession No. CRL 10421. The cell for the 5-HT$_{1D\beta}$receptor, designated as Ltk-11, was deposited on Apr. 17, 1990, and accorded ATCC Accession No. CRL 10422. The cell line for the 5-HT$_{1E}$ receptor, designated 5-HT$_{1E}$-7, was deposited on Nov. 6, 1991, and accorded ATCC Accession No. CRL 10913. The cell line for the 5-HT$_{1F}$ receptor, designated L-5-HT$_{1F}$, was deposited on Dec. 27, 1991, and accorded ATCC Accession No. CRL 10957. The cell line for the 5-HT7 receptor, designated as L-5-HT-4B, was deposited on Oct. 20, 1992, and accorded ATCC Accession No. CRL 11166. These preparations were suspended in 50 mM Tris-HCl buffer (pH 7.4 at 37° C.) containing 10 mM MgCl$_2$, 0.2 mM EDTA, 10 μM pargyline, and 0.1% ascorbate. The affinities of compounds were determined in equilibrium competition binding assays by incubation for 30 minutes at 37° C. in the presence of 5 nM [3H] serotonin. Nonspecific binding was determined in the presence of 10 μM serotonin. The bound radioligand was separated by filtration through GF/B filters using a cell harvester.

Human 5-HT$_2$ Receptor

The coding sequence of the human 5-HT$_2$ receptor was obtained from a human brain cortex cDNA library, and cloned into the cloning site of pCEXV-3 eukaryotic expression vector. This construct was transfected into COS-7 cells by the DEAE-dextran method. Cells were harvested after 72 hours and lysed by sonication in 5 mM Tris-HCl, 5 mM EDTA, pH 7.5. This cell line was deposited with the ATCC on Oct. 31, 1989, designated as L-NGC-5-$HT_2$, and was accorded ATCC Accession No. CRL 10287. The cell lysates were centrifuged at 1000 rpm for 5 minutes at 4° C., and the supernatant was centrifuged at 30,000×g for 20 minutes at 4° C. The pellet was suspended in 50 mM Tris-HCl buffer (pH 7.7 at room temperature) containing 10 mM $MgSO_4$, 0.5 mM EDTA, and 0.1% ascorbate. The affinity of compounds at 5-$HT_2$receptors were determined in equilibrium competition binding assays using [3H] ketanserin (1 nM). Nonspecific binding was defined by the addition of 10 μM mianserin. The bound radioligand was separated by filtration through GF/B filters using a cell harvester.

5-$H_{1A}$ receptor

The cell line for the 5-$HT_{1A}$ receptor, designated 5-HT1A-3, was deposited on May 11, 1995, and accorded ATCC Accession No. CRL 11889. The cDNA corresponding to the 5-$HT_{1A}$ receptor open reading frames and variable non-coding 5'- and 3'-regions, was cloned into the eukaryotic expression vector pCEXV-3. These constructs were transfected transiently into COS-7 cells by the DEAE-dextran method, and harvested after 72 hours. Radioligand binding assays were performed as described above for the 5-$HT_2$ receptor, except that [3H]-8-OH-DPAT was used as the radioligand and nonspecific binding was determined by the addition of 10 μM mianserin.

Human Dopamine $D_2$ Receptors

The affinity of compounds at the D2 receptor were determined using membrane preparations from COS-7 cells transfected with the gene encoding the human $D_2$ receptor. The coding region for the human D2 receptor was obtained from a human striatum cDNA library, and cloned into the cloning site of PCDNA 1 eukaryotic expression vector. The plasmid DNA for the $D_2$ receptor is designated pcEXV-D2, and was deposited on Nov. 6, 1992 under ATCC Accession No. 75344. This construct was transfected into COS-7 cells by the DEAE-dextran method. Cells were harvested after 72 hours and lysed by sonication in 5mM Tris-HCl, 5 mM EDTA, pH 7.5. The cell lysates were centrifuged at 1000 rpm for 5 minutes at 4° C., and the supernatant was centrifuged at 30,000×g for 20 minutes at 4° C. The pellet was suspended in 50 mM Tris-HCl (pH 7.4) containing 1 mM EDTA, 5 mM KCl, 1.5 mM $CaCl_2$, 4 mM $MgCl_2$, and 0.1% ascorbic acid. The cell lysates were incubated with [3H]spiperone (2 nM), using 10 μM (+)Butaclamol to determine nonspecific binding.

Other Dopamine receptors were prepared by known methods. ($D_1$: Dearry et al., Nature, 347, 72, (1990), deposited with the European Molecular Biological Laboratory (EMBL) Genbank as X55760; $D_3$: Sokoloff, P. et al., Nature, 347, 146 (1990), deposited with the European Molecular Biological Laboratory (EMBL) Genbank as X53944; $D_5$: Sunahara, R. K., et al., Nature, 350, 614 (1991), deposited with EMBL Genbank as X58454-HU HD 5DR).

Functional Assays $\alpha_1$-Adrenoceptor-Mediated Phosphoinositide Accumulation in Cultured Cell Lines The agonist activity of test compounds was assayed by measuring their ability to generate phosphoinositide production in cells stably transfected with each of the three cloned human $\alpha_1$-adrenoceptor subtypes. Cells were plated in 96-well plates and grown to confluence. The day before the assay the growth medium was changed to 100 μl of medium containing 1% serum and 0.5 μCi [³H] myo-inositol, and the plates were incubated overnight in a $CO_2$ incubator (5% $CO_2$ at 37° C.). Immediately before the assay, the medium was removed and replaced by 200 μl of PBS containing 10 mM LiCl, and the cells were equilibrated with the new medium for 20 min. During this interval cells were also equilibrated with the antagonist, added as 10 μl aliquot of a 20-fold concentrated solution in PBS.

The [³H] inositol-phosphate (IP) accumulation was started by adding 10 μl of a solution containing the agonist. To the first well 10 μl were added to measure basal accumulation, and 11 different concentrations of agonist were assayed in the following 11 wells of each plate row. All assays were performed in duplicate by repeating the same additions in two consecutive plate rows. The plates were incubated in a $CO_2$ incubator for 1 hr. The reaction was terminated by adding 15 μl of 50% (v/v) trichloroacetic acid (TCA), followed by a 40 min incubation at 4° C.

After neutralizing TCA with 40 μl of 1 M Tris, the content of the wells was transferred to a Multiscreen HV filter plate (Millipore) containing Dowex AG1-X8 (200–400 mesh, formate form). The filter plates were prepared adding 200 μl of Dowex AG1-X8 suspension (50% v/v, water:resin) to each well. The filter plates were placed on a vacuum manifold to wash or eluted the resin bed. Each well was washed 2 times with 200 μl of water, followed by 2×200 μ of 5 mM sodium tetraborate/60 mM ammonium formate. The [3H] IPs were eluted into empty 96-well plates with 200 μl of 1.2 M ammonium formate/0.1 formic acid. The content of the wells was added to 3 mls of scintillation cocktail, and the radioactivity was determined by liquid scintillation counting.

$\alpha_2$-Adrenoceptor-Mediated Inhibition of Forskolin Stimulated Adenylyl Cyclase The agonist activity of test compounds was assayed by measuring their ability to inhibit adenylyl cyclase in cells stably transfected with each of the three cloned human $\alpha_2$-adrenoceptors. LM(tk-) cells expressing the $\alpha_{2A}$- or the $\alpha_{2C}$-, as well as Y1 cells expressing the $\alpha_{2B}$-adrenoceptor were used. The cell line for the $\alpha_{2B}$-adrenoceptor, designated as Ya2B-2, was deposited on May 11, 1995, and accorded ATCC Accession No. CRL 11888. The formation of cyclic AMP was measured in cultures incubated with DMEM containing 1 mM theophylline. Twelve concentrations of the test compounds (from 10 pM to 100 μM) were added to the incubation medium and incubated at 37° C. for 20 min. Following this incubation step, 10 μM forskolin was added to stimulate the formation of cyclic AMP, and the cultures were incubated for another 10 min. The reaction was stopped by replacing the incubation medium with 100 mM HCl . The intracellular levels of cyclic AMP were measured by radioimmunoassay. The data from concentration-response curves was fitted to a four-parameter logistic equation, by non-linear regression analysis, to determine the $pEC_{50}$ and intrinsic activity.

Isolated Tissue Assays

Protocol for the Identification of -Adrenoceptors in Mammalian Urethra from Functional Studies Using a battery of agonists and antagonists which exhibit selectivity among the $\alpha_1$-adrenoceptor subtypes, a pharmacological profile of the receptor which mediates the contractile response to α-agonists in the urethra of male humans, and male and female dogs and rabbits was determined. In addition, similar studies were done using bladder neck tissue from female dogs. In order to identify the specific receptor subtype in each tissue, the pharmacological profile was compared to the profiles for these same drugs at the cloned human $\alpha_{1A}$, $\alpha_{1B}$, or $\alpha_{1C}$ subtypes.

Methods

Tissue samples from the proximal urethra of male humans and male and female rabbits, as well as tissue samples from both the proximal urethra and bladder neck of male and female dogs were cut into transverse strips (3×10 mm) and suspended under 0.5 g tension in Krebs' physiological buffer at 37° C. To determine agonist potency ($pEC_{50}$) and antagonist affinity constants ($pK_B$), concentration-effect curves to the non-selective agonist phenylepherine were constructed in the absence and in the presence of increasing concentrations of the antagonist. Up to four sequential curves were constructed in each tissue. Antagonists were allowed to equilibrate for 1h before each concentration-effect curve, and the drugs were completely washed out in between successive curves. In each experiment, one tissue served as a "time control", in which no antagonist was added so that changes in tissue sensitivity could be assessed as a function of time. In most instances, antagonist $pK_B$ values were determined by Schild analysis (Arunlakshana and Schild, 1959). In instances in which a single concentration of antagonist was used, $pK_B$ values were determined by the equation: $pK_B = \log((CR-1)/[Antagonist])$, where CR is defined as the ratio of the agonist $EC_{50}$ in the presence of the antagonist to that in the absence of the antagonist. In addition to the antagonist studies, the $\alpha_{1C}$-selective agonists A-61603 and SK&F 102652 were used to characterize the receptor subtype in the female dog urethra, and to compare the receptor profiles in the urethra with that in the bladder neck. In these experiments, two concentration effect curves were constructed on each tissue, one in the absence and the second in the presence of prazosin. The $pK_B$ values derived for prazosin using A-61603 and SK&F 102652 as the agonists were compared to the $pK_B$ obtained for prazosin using phenylephrine as the agonist, to verify that each agonist interacted with a common $\alpha_1$-adrenoceptor site.

Determination of -Adrenoceptor Activity in the Isolated Rat Right Atrium

Right atria were removed from rats and placed immediately into oxygenated Krebs solution at 37° C. The Krebs solution was replaced three times at 5 min intervals and the tissues were tensioned three times to 0.5 g. In spontaneously beating atria, a control concentration effect curve to isoprenaline was generated. β-Adrenoceptor-mediated increase in atrial rate were measured as the response. After complete wash out of the isoprenaline, a concentration effect curve was performed using the agonists A-61603, SK&F 102652, and SDZ NVI 085, up to a concentration of 100 μM. If no response was observed, the drug was left in the bath while another concentration-effect curve to isoprenaline was generated. $pEC_{50}$ values for agonists were calculated by logistic curve fitting. The antagonist effects of the test compounds were measured using the dose-ratio method, by comparing the shift in $pEC_{50}$ for isoprenaline.

Results

Table 2 shows the $pK_I$ values determined from binding assays for various antagonists at the cloned human $\alpha_1$-adrenoceptor subtypes and the corresponding $pK_B$ values determined from contractile studies in urethral and bladder neck tissues obtained from human, dog, and rabbit.

Figure 1B:
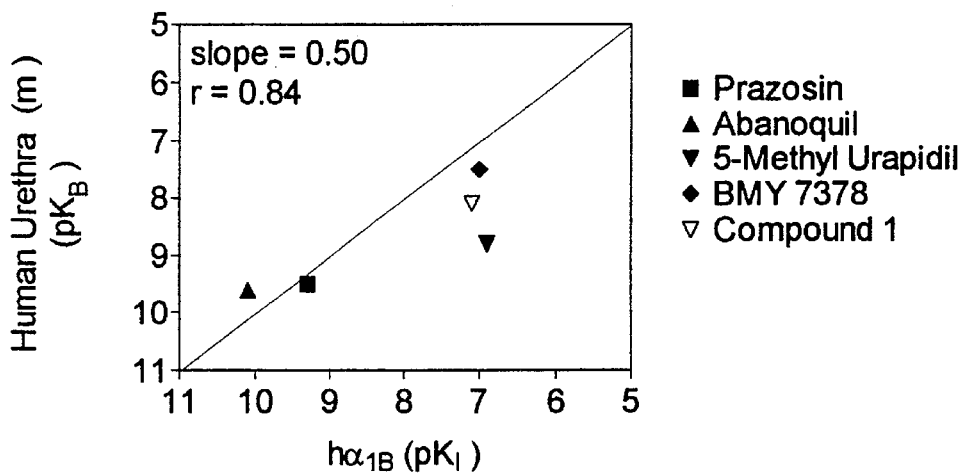
Figure 1C:
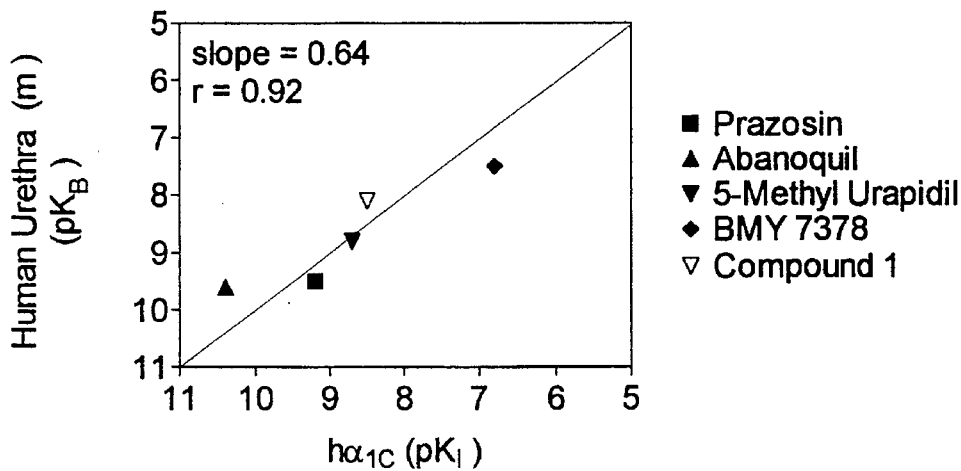
Figure 2A:
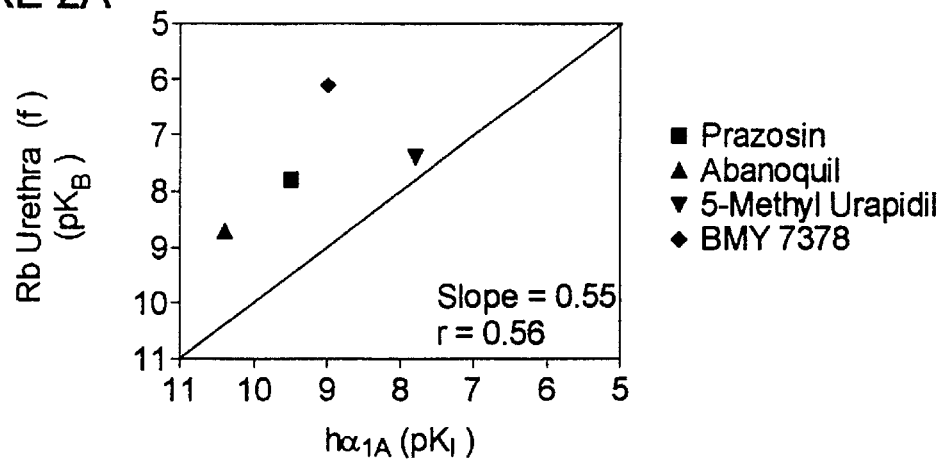
FIGS. 2A, 2B, and 2C show correlation of antagonist $pK_B$ values determined in functional studies of female rabbit urethra versus $pK_I$ values measured in binding experiments using cloned human $\alpha_{1A}$-adrenoceptors (A), $\alpha_{1B}$-adrenoceptors (B), and $\alpha_{1C}$-adrenoceptors (C). The slopes and correlation coefficients (r) for the linear regression analysis are presented in each figure.
Figure 2B:
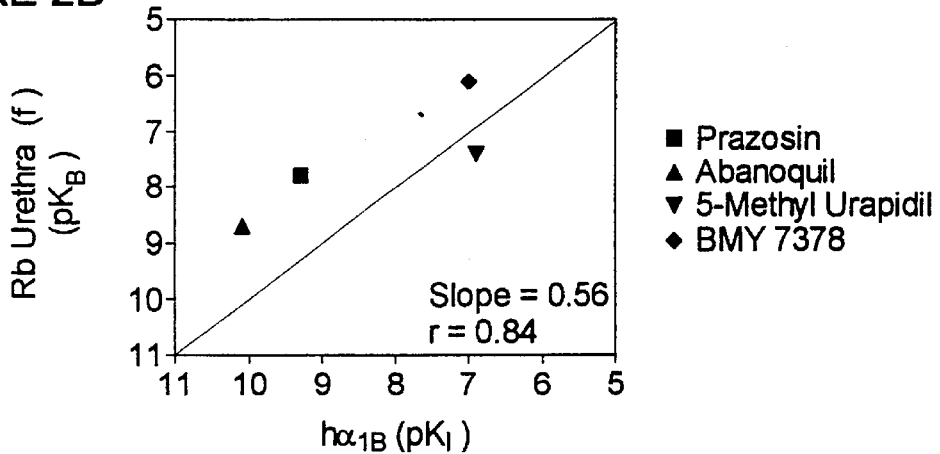
Figure 2C:
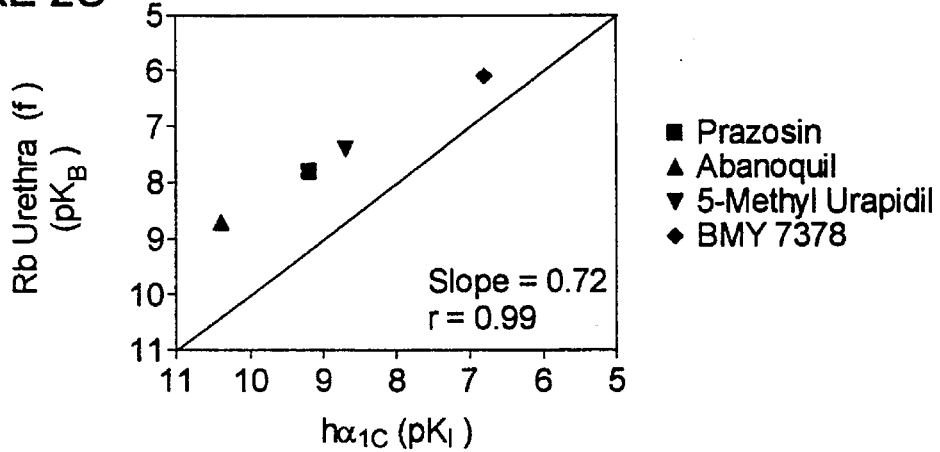
Figure 3A:
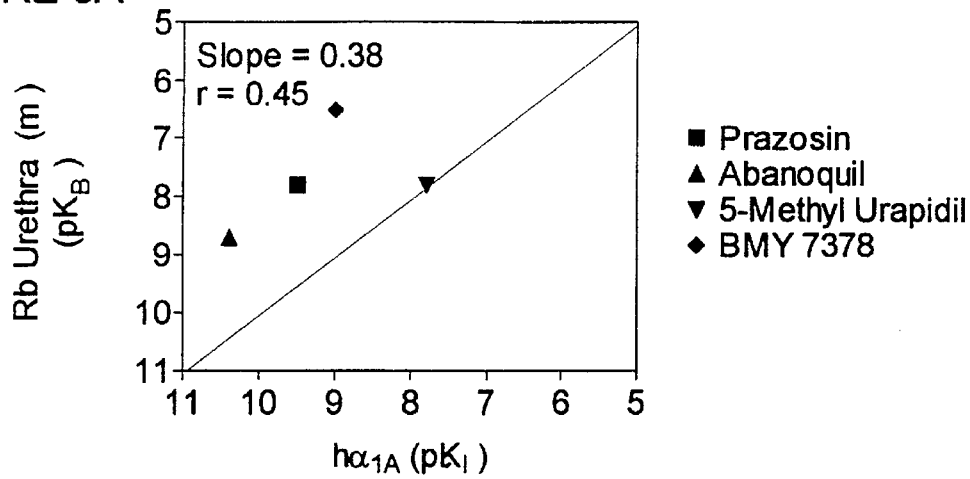
FIGS. 3A, 3B, and 3C show correlation of antagonist $pK_B$ values determined in functional studies of male rabbit urethra versus $pK_I$ values measured in binding experiments using cloned human $\alpha_{1A}$-adrenoceptors (A), $\alpha_{1B}$-adrenoceptors (B), and $\alpha_{1C}$-adrenoceptors (C). The slopes and correlation coefficients (r) for the linear regression analysis are presented in each figure.
Figure 3B:
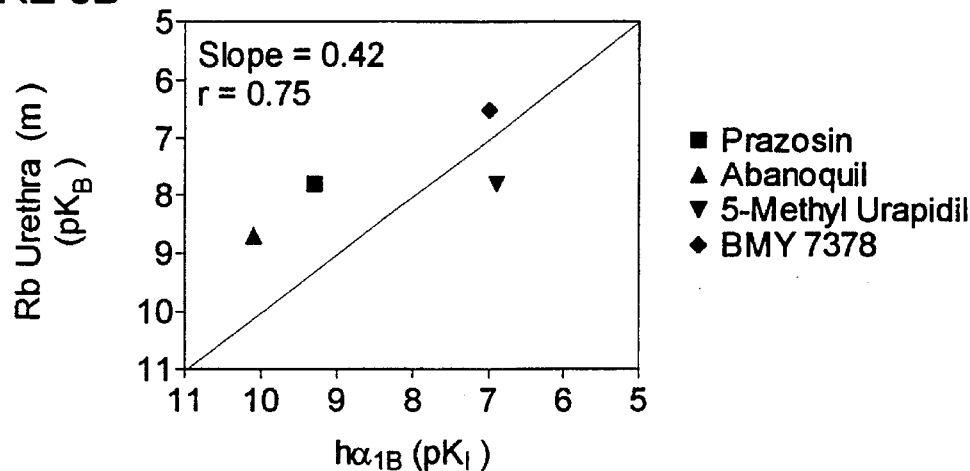
Figure 3C:
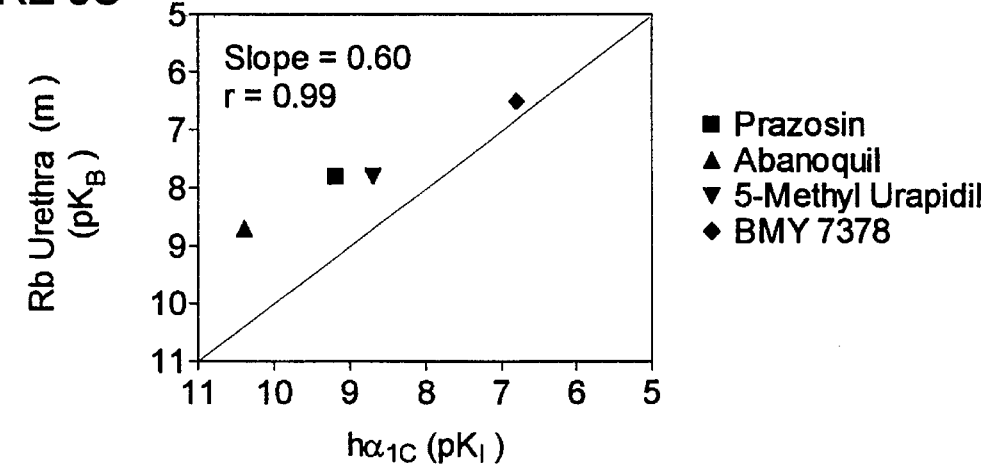
Figure 4A:
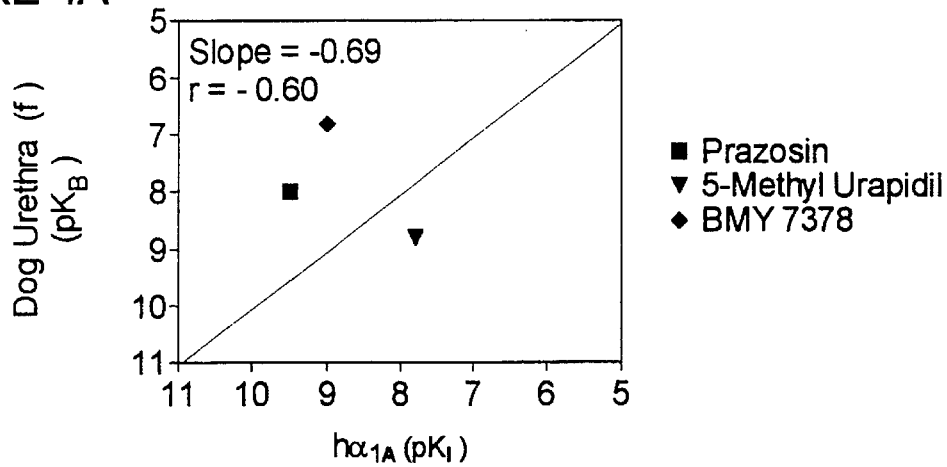
FIGS. 4A, 4B, and 4C show correlation of antagonist $pK_B$ values determined in functional studies of female dog urethra versus $pK_I$ values measured in binding experiments using cloned human $\alpha_{1A}$-adrenoceptors (A), $\alpha_{1B}$-adrenoceptors (B), and $\alpha_{1C}$-adrenoceptors (C). The slopes and correlation coefficients (r) for the linear regression analysis are presented in each figure.
Figure 4B:
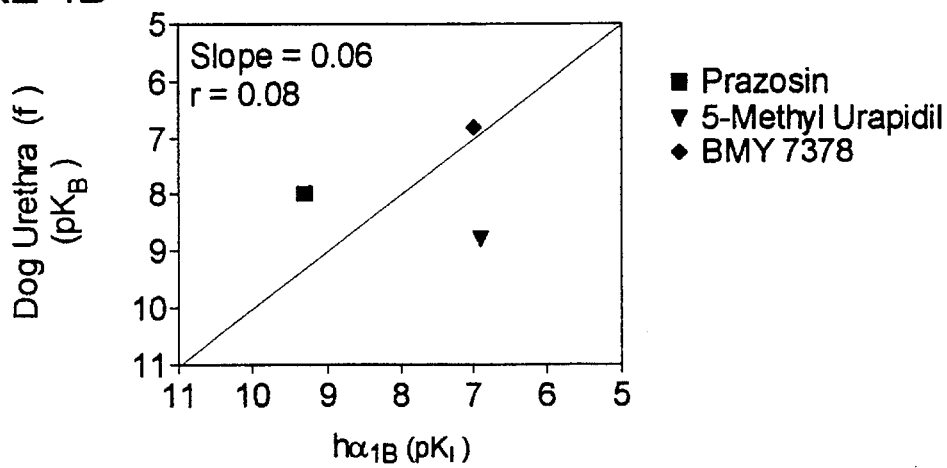
Figure 4C:
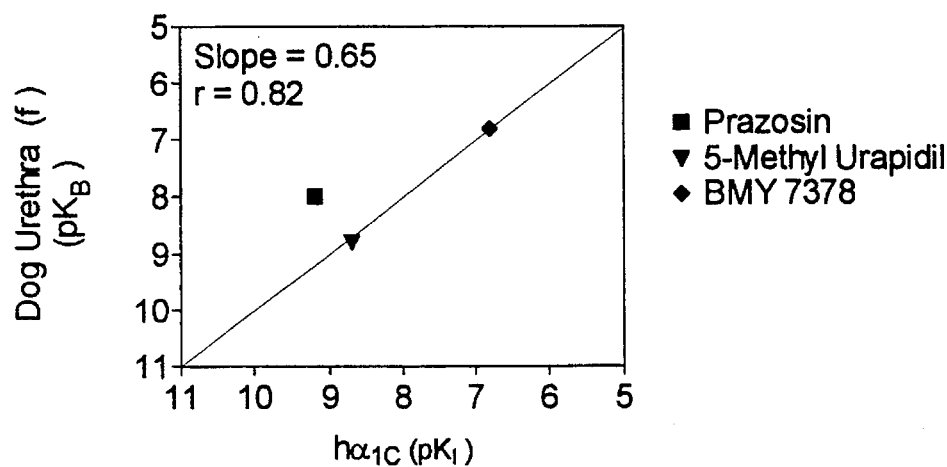
Figure 5A:
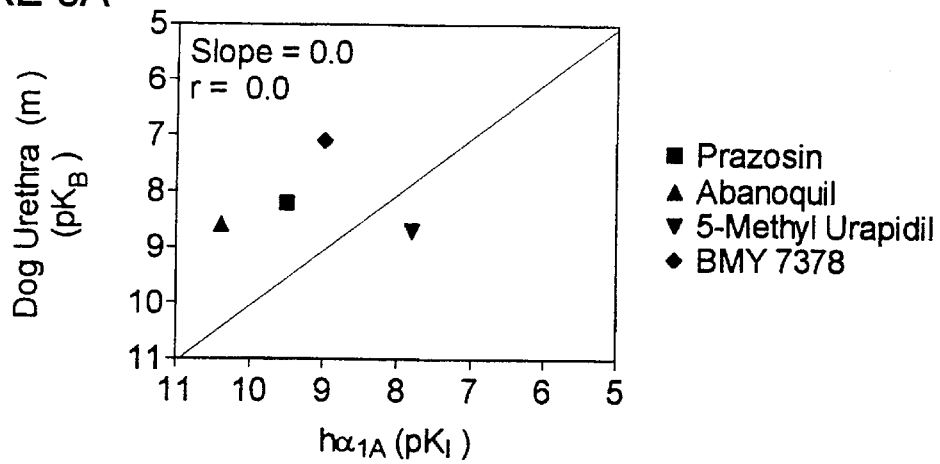
FIGS. 5, 5B, and 5C show correlation of antagonist $pK_B$ values determined in functional studies of male dog urethra versus $pK_I$ values measured in binding experiments using cloned human $\alpha_{1A}$-adrenoceptors (A), $\alpha_{1B}$-adrenoceptors (B), and $\alpha_{1C}$-adrenoceptors (C). The slopes and correlation coefficients (r) for the linear regression analysis are presented in each figure.
Figure 5B:
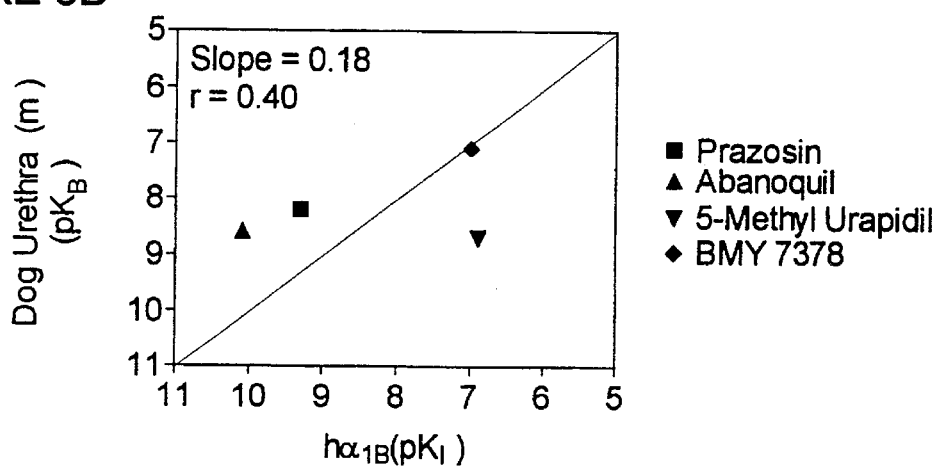
Figure 5C:
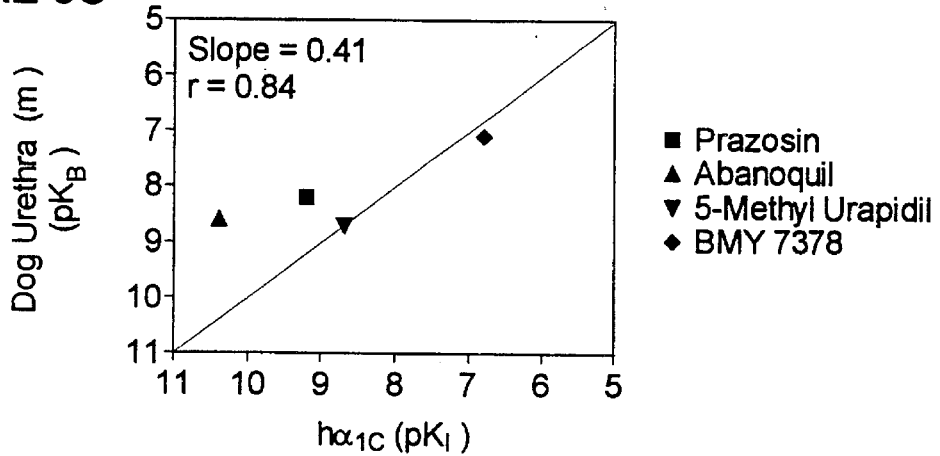
Figure 6:
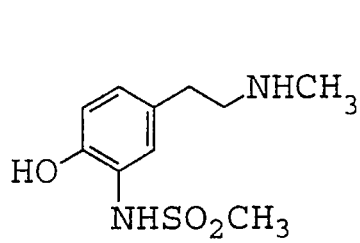
FIG. 6 shows the chemical structures of SK&F 102652, A-61603, SDZ NVI 085, Prazosin, 5-Methyl urapidil, Abanoquil, Compound 1, and ST-1059.
Figure 6:
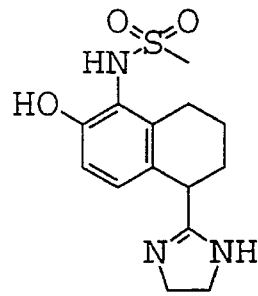
Figure 6:
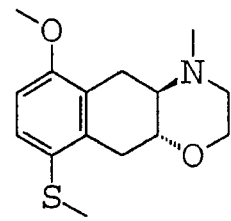
Figure 6:
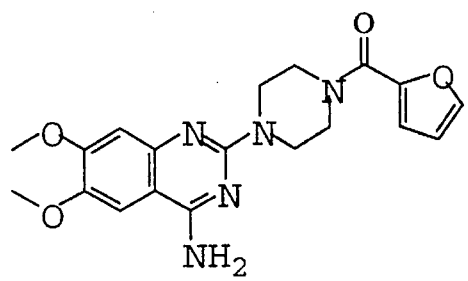
Figure 6:
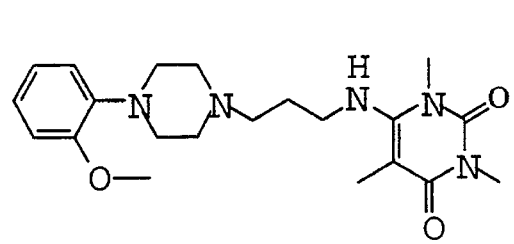
Figure 6:
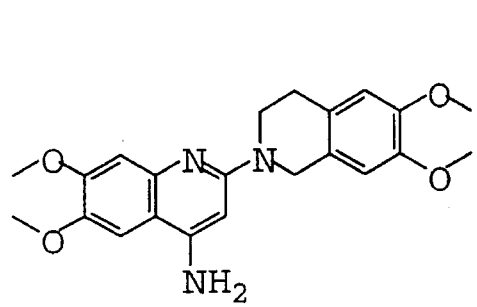
Figure 6:
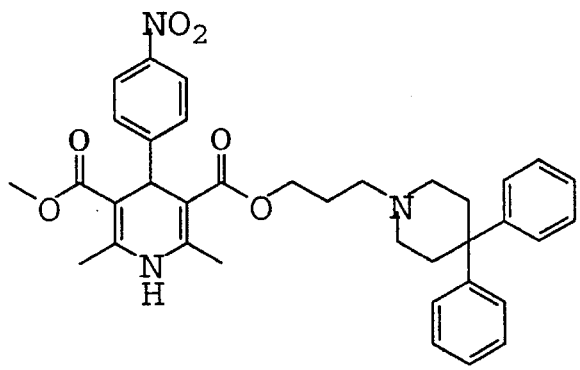
Figure 6:
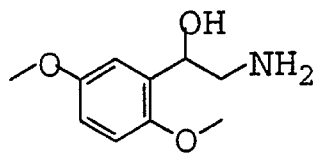

FIGS. 1–5 illustrate the data from Table 2 in a graphical format. For each of the mammalian tissues, the $pK_B$ value for each antagonist (abcissa) is plotted against the $pK_I$ values determined for each of the three cloned human α-adrenoceptor subtypes (ordinate). The slopes and correlation coefficients (r) for the linear regression analysis are presented in each figure. In each case, the antagonist data derived from the functional experiments correlates best with the $\alpha_{1C}$-subtype.

Table 3 shows the $pK_I$, $pEC_{50}$, and intrinsic activity at the cloned $\alpha_1$- and $\alpha_2$-subtypes for the various agonists. In particular, A-61603 and SK&F 102652 each fully stimulate inositol phosphate production in cells transfected with the human $\alpha_{1C}$-adrenoceptor, but are virtually inactive at the $\alpha_{1A}$- and $\alpha_{1B}$-subtypes. Table 3 also indicates that while both A-61603 and SK&F 102652 are selective among the $\alpha_1$-adrenoceptors, these compounds also possess significant activity at $\alpha_2$-adrenoceptors. The cross-reactivity binding profiles of these drugs and other agonists are shown in Table 4.

Because of the ability of A-61603 and SK&F 102652 to fully stimulate $\alpha_{1C}$-adrenoceptors, but not $\alpha_{1A}$- or $\alpha_{1B}$-subtypes, these compounds were used in the female dog tissues to compliment the antagonist-based pharmacological characterization. Additionally, these two compounds were used to establish that the $\alpha_1$-subtype in the urethra is identical to the $\alpha_1$-subtype in the bladder neck. The potency of these agonists and the $PK_B$ value for prazosin in antagonizing their effects in each tissue are as follows:

| Bladder Neck | $pEC_{50}$ | Prazosin $pK_B$ |
| --- | --- | --- |
| A-61603 | 6.8 | 8.3 |
| SK&F 102652 | 5.7 | 7.8 |

| Urethra | $pEC_{50}$ | Prazosin $pK_B$ |
| --- | --- | --- |
| A-61603 | 6.7 | 8.3 |
| SK&F 102652 | 6.0 | 8.5 |

In each tissue, the magnitude of the contractions produced by A-61603 and SK&F 102652 was similar to the magnitude of the contraction produced by phenylephrine. In addition, the contractions produced by A-61603 and SK&F 102652 were highly sensitive to prazosin, confirming their action at an $\alpha_1$-adrenoceptor site. The high degree of selectivity of these compounds for the $\alpha_{1C}$-subtype over the $\alpha_{1A}$ and $\alpha_{1B}$ subtypes, indicates that it is the $\alpha_{1C}$-subtype which mediates contraction of the urethra as well as the bladder neck.

TABLE 2

Antagonist affinities ($pK_1$ versus $^3$H-prazosin binding) at human cloned $\alpha_1$-adrenoceptors and antagonist affinities determined from contractile studies ($pK_B$ versus phenylephrine-induced contraction) in urethra and bladder neck (BN) tissue from mammalian species. (* 5-methyl urapidil)

| | Human Clones | | | Human Urethra Male | Rabbit Urethra Male | Rabbit Urethra Female | Dog BN Male | Dog BN Female |
| --- | --- | --- | --- | --- | --- | --- | --- | --- |
| Antagonist | h$\alpha_{1A}$ | h$\alpha_{1B}$ | h$\alpha_{1C}$ | | | | | |
| Prazosin | 9.5 | 9.3 | 9.2 | 9.5 | 7.8 | 7.8 | 8.2 | 8.0 |

TABLE 2-continued

Antagonist affinities (pK₁ versus ³H-prazosin binding) at human cloned α₁-adrenoceptors and antagonist affinities determined from contractile studies (pK$_B$ versus phenylephrine-induced contraction) in urethra and bladder neck (BN) tissue from mammalian species. (* 5-methyl urapidil)

| | Human Clones | | | Human Urethra Male | Rabbit Urethra Male | Rabbit Urethra Female | Dog BN Male | Dog BN Female |
|---|---|---|---|---|---|---|---|---|
| Abanoquil | 10.4 | 10.1 | 10.4 | 9.6 | 8.7 | 8.7 | 8.6 | — |
| 5-MU * | 7.8 | 6.9 | 8.7 | 8.8 | 7.8 | 7.4 | 8.7 | 8.8 |
| BMY 7378 | 9.0 | 7.0 | 6.8 | 7.5 | 6.5 | 6.1 | 7.1 | 6.8 |
| Compound 1 | 6.5 | 7.1 | 8.5 | 8.1 | — | — | 6.2 | — |

TABLE 3

Pharmacological profiles of agonists at cloned human α-adrenoceptors. Binding affinity (pKi), potency (pEC$_{50}$), and intrinsic activity were determined as described in the in the text.

| Compound | | α$_{1A}$ | α$_{1B}$ | α$_{1C}$ | α$_{2A}$ | α$_{2B}$ | α$_{2C}$ |
|---|---|---|---|---|---|---|---|
| (−)-ephedrine | pKi | 4.3 | 4.0 | 4.6 | 6.1 | 5.6 | 5.1 |
| | pEC$_{50}$ | 4.0 | 4.0 | 4.0 | 6.6 | 6.6 | 5.0 |
| | i.a. | 0.1 | 0.2 | 0.1 | 0.3 | 0.4 | 0.0 |
| (−)-norephedrine | pKi | 4.6 | 4.3 | 4.8 | 6.3 | 6.6 | 5.5 |
| | pEC$_{50}$ | 4.8 | 4.5 | 4.3 | 8.1 | 6.1 | 6.9 |
| | i.a. | 0.3 | 0.0 | 0.4 | 0.5 | 0.5 | 0.6 |
| (−)-phenyle-phrine | pKi | 5.4 | 4.7 | 4.1 | 6.9 | 6.4 | 6.4 |
| | pEC$_{50}$ | 5.9 | 5.7 | 5.9 | 6.9 | 6.9 | 6.4 |
| | i.a. | 0.7 | 0.9 | 0.9 | 1.0 | 0.8 | 0.9 |
| ST-1059 | pKi | 5.1 | 4.9 | 5.1 | 5.7 | 5.8 | 5.4 |
| | pEC$_{50}$ | 5.8 | 5.2 | 5.7 | 5.6 | 8.6 | 6.3 |
| | i.a. | 0.1 | 0.1 | 0.9 | 0.2 | 0.6 | 0.5 |
| A-61603 | pKi | 4.9 | 4.8 | 7.1 | 7.3 | 6.5 | 6.2 |
| | pEC$_{50}$ | 4.6 | 4.4 | 8.9 | 7.5 | 7.1 | 7.7 |
| | i.a. | 0.1 | 0.1 | 1.2 | 0.8 | 0.8 | 0.9 |
| SK&F 102652 | pKi | 4.9 | 4.4 | 5.6 | 6.4 | 6.5 | 5.8 |
| | pEC$_{50}$ | 4.7 | 4.3 | 6.9 | <4.0 | 7.5 | 7.1 |
| | i.a. | 0.1 | 0.1 | 1.1 | 0.0 | 0.9 | 0.8 |
| SDZ NVI-085 | pKi | 5.7 | 4.9 | 5.9 | 7.3 | 7.2 | 6.1 |
| | pEC$_{50}$ | <4.0 | <4.0 | 6.4 | <4.0 | <4.0 | <4.0 |
| | i.a. | 0.0 | 0.0 | 1.1 | 0.0 | 0.0 | 0.0 |

TABLE 4

Cross-reactivity receptor binding profiles at human cloned histamine subtypes (H1, H2), dopamine subtypes (D1, D2, D3, D5), and serotonin subtypes (5-HT: 1A, 1Dα, 1Dβ, 1E, 1F, 2, 7), as well as rat atrial β-adrenoceptors. Affinities (pKi) were determined as described in the text.

| Compound | H1 | H2 | D1 | D2 | D3 | D5 | 1A | 1Dα | 1Dβ | 1E | 1F | 2 | 7 | β |
|---|---|---|---|---|---|---|---|---|---|---|---|---|---|---|
| A-61603 | 4.3 | 48 | 4.7 | 5.0 | 5.8 | 4.8 | 5.4 | 5.6 | 5.2 | 5.3 | 5.3 | 4.3 | 5.3 | <4 |
| SK&F 102652 | 4.3 | 4.6 | 5.0 | 6.7 | 6.7 | 4.8 | 5.8 | 5.9 | 5.5 | 5.3 | 5.3 | 4.8 | 5.3 | <4 |
| SDZ NVI-085 | 5.3 | 5.2 | 5.1 | 5.5 | 6.0 | 4.7 | 7.1 | 7.9 | 7.7 | 5.7 | 7.0 | 6.5 | 7.0 | <4 |

References

Abel, P. W. et al. (1995) The atypical alpha-1-adrenoceptor. *Pharmacol. Comm.*, 6, 29–38.

Andersson, K.-E. and Sjögren, C. (1982) Aspects on the physiology and pharmacology of the bladder and urethra. *Progress in Neurobiology*, 19, 71–89.

Ariens, E. J. et al., (1960) Receptor reserve and threshold phenomena. *Arch Int Pharmacdyn Ther*, 127,459–478.

Arunlakshana, O. and Schild, H. O. (1959) Some quantitative uses of drug antagonists. *Br J Pharacol Chemother*, 14, 48–58.

Chess-Williams, R. et al. 1994) Alpha-1A-adrenoceptor subtype mediates contraction of the rat urethra. *J Auton Pharmacol*, 14, 375–381.

Bylund, D. B. (1992) *FASEB J*, 6, 832.

Cheng, Y. -C. and Prusoff, W. H. (1973) *Biochem Pharmacol*, 22, 3099–3108.

Forray, C. et al. (1994) The alpha-1-adrenoceptor that mediates smooth muscle contraction in human prostate has the pharmacological properties of the cloned human alpha-1C subtype. *Mol Pharmacol*, 45, 703–708.

Hatano, A. et al. (1994) Pharmacological evidence of distinct alpha-1-adrenoceptor subtypes mediating the contraction of human prostatic urethra and peripheral artery. *Brit J Pharmacol*, 113, 723–728.

Johnson, D. A. (1991) Pharmacology and safety of phenylpropanolamine. *Drug Development Research* 22,197–207.

Kenakin, T. P. (1987) In: *Pharmacological Analysis of Drug-Receptor Interaction*. pp 190–192, Raven Press, New York.

Latifpour, J. (1990) Autonomic receptors in urinary tract: sex and age differences. *J Pharmacol Exp Ther*, 253, 661–667.

Lopata et al. (1984) High-level expression of a chloramphenicol acetyltransferase gene by DEAE-dextran-mediated DNA transfection coupled with a dimethyl sulfoxide or glycerol shock treatment. *Nucl. Acids Res.*, 12, 5707–5717.

Muramatsu, I. et al. (1995) Functional subclassification of vascular alpha-1-adrenoceptor. *Pharmacol. Comm.*, 6, 23–28.

Receptor and Ion Channel Nomenclature Supplement (1995) *Trends Pharmacol Sci.*, p 9.

Sand, P. K. et al., (1990) Advances in nonoperative treatment of genuine stress incontinence. *Current Opinion in Obstetrics and Gynecology*, 2, 599–604.

Sourander, L. B. (1990) Treatment of urinary incontinence: The place of drugs. *Gerontology* 36, 19–26.

Testa, R. et al. (1993) Characterization of alpha-1 adrenoceptor subtypes in prostate and prostatic urethra of rat, rabbit, dog, and man. *Eur J Pharmacol* 249, 307–315.

Tsujimoto, G. et al., (1986) Alpha adrenoceptors in the rabbit bladder base smooth muscle: alpha-1 adrenoceptors mediate contractile responses. *J Pharmacol Exp Ther*, 228, 384–389.

Lundberg, G. D. (editor) Urinary Incontinence Consensus Conference (1989) Urinary incontinence in adults. JAMA 261, No. 18, 2685–2690.

Walters, M. D. et al., (1992) Nonsurgical treatment of urinary incontinence. *Current Opinion in Obstetrics and Gynecology*, 4, 554–558.

Watson, S. and Girldstone, D., (1995) Receptor and Ion Channel Nomenclature Supplement, *Trends Pharmacol Sci.* 1995 *Receptor and Ion Channel Nomenclature Supplement*, 9–12.

Wein, A. J. (1987) Lower urinary tract function and pharmacologic management of lower urinary dysfunction. *Urologic Clinics of North America*, 14, 273–296.

Willette, R. N. et al. (1990) Role of alpha-1 and alpha-2 adrenoceptors in sympathetic control of the proximal urethra. *J Pharmacol Exp Ther* 252, 706–710.

Yablonsky, F. et al. (1986) Alpha-1 and alpha-2 adrenoceptors in the smooth muscle of male and female rabbit urethra. *Eur J Pharmacol* 121, 1–8.

Yoshida, M. et al. (1991) Pharmacological characterization of alpha-adrenoceptors in the young and old female rabbit urethra. *J Pharmacol Exp Ther* 257, 1100–1108.

What is claimed:

1. A method of treating urinary incontinence in a subject which comprises administering to the subject a therapeutically effective amount of a compound having the structure:

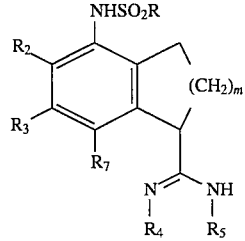

wherein m is an integer from 0 to 2; wherein each of $R_2$, $R_3$ and $R_7$ is independently H; OR; R; halo; amino; or acetamido; wherein R is H or $C_1$–$C_6$ alkyl; wherein $R_3$ and $R_7$ taken together constitute a methylenedioxy, ethylenedioxy, benzimidazole or indole ring; wherein each of $R_4$ and $R_5$ are independently H or taken together has the following formula:

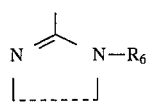

wherein the dashed line represents a single or double bond; and $R_6$ is H or $C_1$–$C_6$ alkyl; or a pharmaceutically acceptable salt thereof.

2. The method of claim 1, wherein the compound has the structure:

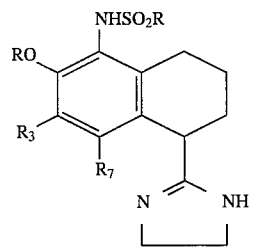

3. The method of claim 2, wherein the compound has the structure:

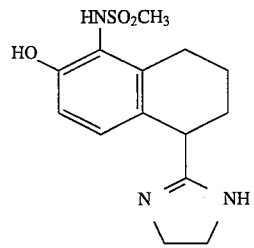

* * * * *

UNITED STATES PATENT AND TRADEMARK OFFICE
CERTIFICATE OF CORRECTION

PATENT NO. : 5,610,174
DATED : March 11, 1997
INVENTOR(S) : Douglas A. Craig, Carlos C. Forray, Charles Gluchowski, Theresa A. Branchek It is certified that error appears in the above-identified patent and that said Letters Patent is hereby corrected as shown below:

On the title page, item [54] and column 1,
    In the title: "$\alpha_{1A}$" should read --$\alpha_{1C}$--
    column 7, line 8: "c" should read --$\alpha_{1c}$--
    column 18, line 40: "$CH_2C_2$" should read --$CH_2Cl_2$--
        line 64: "$CH_2C_2$" should read --$CH_2Cl_2$--
        line 65: "$CH_2C_2$" should read --$CH_2Cl_2$--
    column 25, line 34: "-Adrenoceptor" should read --$\beta$-Adrenoceptor--

Signed and Sealed this

Second Day of February, 1999

Attest:

*Attesting Officer*

*Acting Commissioner of Patents and Trademarks*